United States Patent
Rushing

(10) Patent No.: US 11,185,385 B1
(45) Date of Patent: Nov. 30, 2021

(54) AXIS ALIGNING, FORCE-LIMITING FORCEPS

(71) Applicant: Calvin J. Rushing, Plantation, FL (US)

(72) Inventor: Calvin J. Rushing, Plantation, FL (US)

(*) Notice: Subject to any disclaimer, the term of this patent is extended or adjusted under 35 U.S.C. 154(b) by 445 days.

(21) Appl. No.: 16/197,656

(22) Filed: Nov. 21, 2018

Related U.S. Application Data

(60) Provisional application No. 62/589,923, filed on Nov. 22, 2017.

(51) Int. Cl.
| | | |
|---|---|---|
| *A61B 17/28* | (2006.01) | |
| *A61B 17/29* | (2006.01) | |
| *A61B 90/00* | (2016.01) | |
| *A61B 17/66* | (2006.01) | |

(52) U.S. Cl.
CPC ............ *A61B 90/03* (2016.02); *A61B 17/282* (2013.01); *A61B 17/2816* (2013.01); *A61B 17/2833* (2013.01); *A61B 17/2841* (2013.01); *A61B 17/66* (2013.01); *A61B 2090/032* (2016.02); *A61B 2090/065* (2016.02)

(58) Field of Classification Search
CPC . A61B 90/03; A61B 17/2833; A61B 17/2816; A61B 17/282; A61B 17/2841; A61B 17/66; A61B 2090/032; A61B 2090/065
See application file for complete search history.

(56) References Cited

U.S. PATENT DOCUMENTS

| | | | | |
|---|---|---|---|---|
| 3,696,662 A | * | 10/1972 | Foltz | ............ G01N 3/40 73/81 |
| 3,785,381 A | * | 1/1974 | Lower | .......... G01L 5/0028 606/122 |
| 4,432,376 A | * | 2/1984 | Huszar | ............... A61B 5/227 33/784 |

* cited by examiner

*Primary Examiner* — Anh T Dang
(74) *Attorney, Agent, or Firm* — John Rizvi; John Rizvi, P.A.

(57) ABSTRACT

An axis-aligning, force-limiting periarticular/intraarticular reduction forceps suitable for the reduction and realignment of specific anatomic structures includes a pair of medial and lateral forceps tines. A pair of tine tips may terminate the forceps tines, respectively. A pair of lateral and medial forceps handles may extend from the medial and lateral forceps tines, respectively. A first tine/handle junction may attach the lateral forceps handle to the medial forceps tine. A second tine/handle junction may attach the medial forceps handle to the lateral forceps tine. The second tine/handle junction may be pivotally attached to the first tine/handle junction. A force quantifying and limiting mechanism limits the magnitude of clamping force the medial and lateral forceps handles apply to the medial and lateral forceps tines. A pair of X-ray-visible targets on the medial and lateral tines assist with axis alignment for the insertion of fixation devices.

17 Claims, 16 Drawing Sheets

AXIS ALIGNING, FORCE-LIMITING FORCEPS

CROSS-REFERENCE TO RELATED APPLICATION

This application claims the benefit of U.S. Provisional Patent Application Ser. No. 62/589,923, filed on Nov. 22, 2017, which is incorporated herein in its entirety.

FIELD OF THE INVENTION

The present invention relates generally to medical devices, and more particularly, to axis aligning, force-limiting periarticular/intraarticular reduction forceps suitable for the reduction and realignment of specific anatomic structures (osseous/soft tissue) either by means of open reduction and internal fixation, or percutaneous fixation with or without closed reduction.

BACKGROUND OF THE INVENTION

In surgery, the grasping, pulling and handling of tissues is often necessary. A surgeon frequently uses forceps for the purpose of grasping anatomic structures in order to move the structures out of the way or appose the structures for realignment/fixation. However, it is often important for the surgeon to apply the correct magnitude of force to the forceps during the movement of the structures, particularly in the case of grasping and handling periarticular tissue, whose realignment can directly affect the intra-articular contact mechanics (area, force, pressure) of joints in close proximity. If the surgeon applies insufficient force to the tissue through the forceps, displacements/malreduction from undercompression may result, leading to poorer patient outcomes, altered joint contact mechanics, and degenerative arthritis. Application of excessive force to the tissue, on the other hand, may result in damage to the tissue with resulting displacements/malreduction from overcompression, with similar negative sequela. Particularly in the case of periarticular structures such as the distal tibiofibular syndesmosis/ankle syndesmosis, which possess an intricate relationship with major WB joints including the tibiotalar/ankle joint, application of the correct magnitude of pressure during the surgical procedure is critical.

Commercially available periarticular/intraarticular reduction forceps, also referred to as reduction clamps, include pelvic periarticular reduction forceps and Weber clamps. These commercial devices commonly utilize a ratcheting mechanism to apply and maintain pressure on anatomic structures during reduction, realignment and fixation procedures, i.e. procedures involving reducing the size of an anatomic structure or tissue (e.g. a broken bone), realigning the anatomic structure or tissue to its native orientation (e.g. correct repositioning of the bone prior to healing) and placement of at least one fixation device (e.g., screw) to maintain the realigned anatomic structure or tissue in the realigned position. However, these commercial devices may fail to precisely quantitate and limit the subjective force which is applied to the anatomic structures by the operating surgeon during reduction, realignment and fixation procedures. Moreover, low profile tines on the reduction clamps do not assist surgeons in accurately identifying the desired transmalleolar/centroidal axis for orienting the screw or other fixation device on insertion. As a result, malreduction of the aligned segments of an anatomical structure secondary to the applied force, and inappropriate initial fixation device orientation, may occur in certain instances. This malreduction may be particularly evident in repairing injuries of the distal tibiofibular syndesmosis, a slightly movable articulation composed of contiguous surfaces of the tibia/fibula which are united by a ligamentous complex, which plays an integral role in the contact mechanics and function of the ankle joint. Injury to this structure may occur in isolation, or more commonly, in association with osseous ankle fractures (Weber B or C) or associated ankle injuries, with or without dislocation.

The distal tibiofibular syndesmosis is highly sensitive to intraoperative forceps/clamp forces applied in the coronal plane during surgical repair of the structure. Here, the varying subjective force which is applied between surgeons who utilize commercially-available reduction systems can directly lead to iatrogenic coronal plane over-compression (>1 mm fibular medicalization) or under-compression (>1 mm fibular lateralization observed on axial computed tomography 10 mm proximal to the distal tibial plafond) and secondarily indirect iatrogenic malreduction in other planes (sagittal, anterior-posterior/axial, internal-external). The incidence of iatrogenic syndesmotic coronal plane malreduction has been reported to be as high as 52%, and the subjective force applied among surgeons has varied from 36 N to 261 N in one investigation. Iatrogenic malreduction in the sagittal and axial planes with commercially available reduction devices is also particularly problematic, owing to the inherent difficulties in identifying the appropriate placement of the reduction clamp tines along the transmalleolar/centroidal axis and off axis trajectories of the fixation devices (screw, etc.) relative to the surgeon's desired axis. In many instances, surgeons are left to use their best intraoperative judgement to achieve the desired alignment of the fixation device along the transmalleolar/centroidal axis, which has been identified to be approximately of 20-30 degrees off the coronal plane, or between the peroneal ridge of the fibula laterally, and a meanpoint 4 mm anterior to the tibia's midline medially, 10-15 mm proximal to the distal tibial plafond. This is achieved by aiming the screw(s) orientation sufficiently from a posterolateral on the fibula, to an anteromedial position on the tibia at varying distances from the ankle joint line. However, the inherent variability in the patient's limb position on the operating room table alters (external rotation increases/internal rotation decreases) the fixation device's ideal trajectory, leaving surgeons to rely on their best subjective judgement under fluoroscopy, and frequently results in iatrogenic sagittal and/or axial plane malreduction. Saliently, accurate anatomic reduction of the distal tibiofibular syndesmosis is one of the most important predictors of patient outcome following syndesmotic injury. Malreduction is correlated with altered ankle joint contact mechanics (area, force, pressure), poorer functional outcome measures (pain, functional disability), limited ankle joint range of motion, impingement, early onset ankle arthrosis, and the need for additional operations. Clearly, accurate intraoperative reduction of the distal tibiofibular syndesmosis is currently limited with the commercially-available devices.

Accordingly, there is an established need for a solution to at least one of the aforementioned problems. For example, there remains a need for a periarticular/intraarticular reduction forceps suitable for the reduction and realignment of specific anatomic structures (osseous/soft tissue) either by means of open reduction and internal fixation or percutaneous fixation with or without closed reduction, where the reduction forceps is capable of quantifying and self-limiting the force applied to the anatomic structure. There is also a need for a solution which guides the surgeon in correctly placing syndesmotic fixation deices along the desired transmalleolar/centroidal axis/axes following application of the reduction clamp.

SUMMARY OF THE INVENTION

The present invention is directed to axis aligning, force-limiting periarticular/intraarticular reduction forceps suitable for the reduction and realignment of specific anatomic structures (osseous/soft tissue) either by means of open reduction and internal fixation or percutaneous fixation with or without closed reduction. The force-limiting periarticular/intraarticular reduction forceps may include a pair of medial and lateral forceps tines. A pair of tapered or pointed tine tips may terminate the forceps tines, respectively. A pair of lateral and medial forceps handles may extend from the respective medial and lateral forceps tines at respective first and second tine/handle junctions. A force quantifying and limiting mechanism limits the magnitude of clamping force which the forceps handles apply to the forceps tines and enable the operator of the forceps to fully engage the forceps handles without over-compression of the anatomical structure to which the forceps tines are applied. This expedient may reduce the incidence of iatrogenic syndesmotic coronal plane malreduction.

In a first implementation of the invention, a reduction forceps suitable for the reduction and realignment of specific anatomic structures comprises a medial forceps tine and a lateral forceps tine, terminated in a pair of tine tips. The reduction forceps further includes a lateral forceps handle and a medial forceps handle extending from the medial forceps tine and lateral forceps tine, respectively. A first tine/handle junction attaches the lateral forceps handle to the medial forceps tine. Similarly, a second tine/handle junction attaches the medial forceps handle to the lateral forceps tine. The first and second tine/handle junctions are pivotally attached to one another about a rotation axis. The reduction forceps further includes a force quantifying and limiting mechanism configured to limit the magnitude of clamping force applied by the medial and lateral forceps tines.

In a second aspect, the force quantifying and limiting mechanism can include a mechanical pressure gauge configured to be actuated responsively to pivoting the medial forceps handle and lateral forceps handle relative to one another about the rotation axis.

In another aspect, the force quantifying and limiting mechanism can further include a pusher configured to push a button on the mechanical pressure gauge responsively to pivoting the medial forceps handle and lateral forceps handle toward one another about the rotation axis.

In another aspect, the mechanical pressure gauge can be carried by one of the lateral forceps handle and the medial forceps handle, and the pusher can be carried by the other of the lateral forceps handle and the medial forceps handle.

In another aspect, the mechanical pressure gauge can be carried by the lateral forceps handle and the pusher is carried by the medial forceps handle.

In another aspect, an angular distance between the pusher and the mechanical pressure gauge can be adjustable.

In another aspect, the mechanical pressure gauge can be carried by one of the lateral forceps handle and the medial forceps handle, and the pusher can be carried by a first arc-shaped arm comprised in the other of the lateral forceps handle and the medial forceps handle. The first arc-shaped arm can extend towards the mechanical pressure gauge.

In another aspect, the position of the pusher along the first arc-shaped arm can be adjustable to vary the angular distance between the pusher and the mechanical pressure gauge.

In another aspect, said one of the lateral forceps handle and the medial forceps handle carrying the mechanical pressure gauge can include a second arc-shaped arm disposed overlapping the first arc-shaped arm. The first and second arc-shaped arms can be interlockable with one another to prevent a relative movement thereof and thereby prevent rotation of the medial and lateral forceps tines and the lateral and medial forceps handles about the rotation axis.

In another aspect, the pusher can include a pusher body and an attachment plate, the pusher body extending through the first and second arc-shaped arms and comprising a shoulder portion. The shoulder portion and attachment plate can be arranged on opposite sides of the first and second arc-shaped arms and can be configured to press against the first and second arc-shaped arms and frictionally prevent a relative movement of the first and second arc-shaped arms.

In another aspect, the first and second arc-shaped arms can include respective first and second arc-shaped slots that overlap with one another. The pusher body can extend through the first and second arc-shaped slots.

In another aspect, the pusher can be fixable at different angular positions along the second arc-shaped slot to vary the angular distance between the pusher and the mechanical pressure gauge.

In another aspect, the second arc-shaped arm can include a set of angularly-spaced-apart openings. The pusher can be selectively fixable to different openings to vary the angular distance between the pusher and the mechanical pressure gauge.

In another aspect, the reduction forceps can further include a pair of target portions arranged at the tine tips, wherein the target portions are visible by X-ray imaging such as, but not limited to, fluoroscopy.

In another aspect, the target portions can be oriented such that the target portions are aligned in a direction parallel to a direction of alignment of the tine tips.

In another aspect, at least one of the target portions is height-adjustable.

In another aspect, at least one of the target portions can be removable from the corresponding tine tip.

In another aspect, the force quantifying and limiting mechanism can include a visual indicator of the magnitude of clamping force applied by the medial and lateral forceps tines. For instance and without limitation, the visual indicator can include a dial actuated by the mechanical pressure gauge.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

Figure 1:
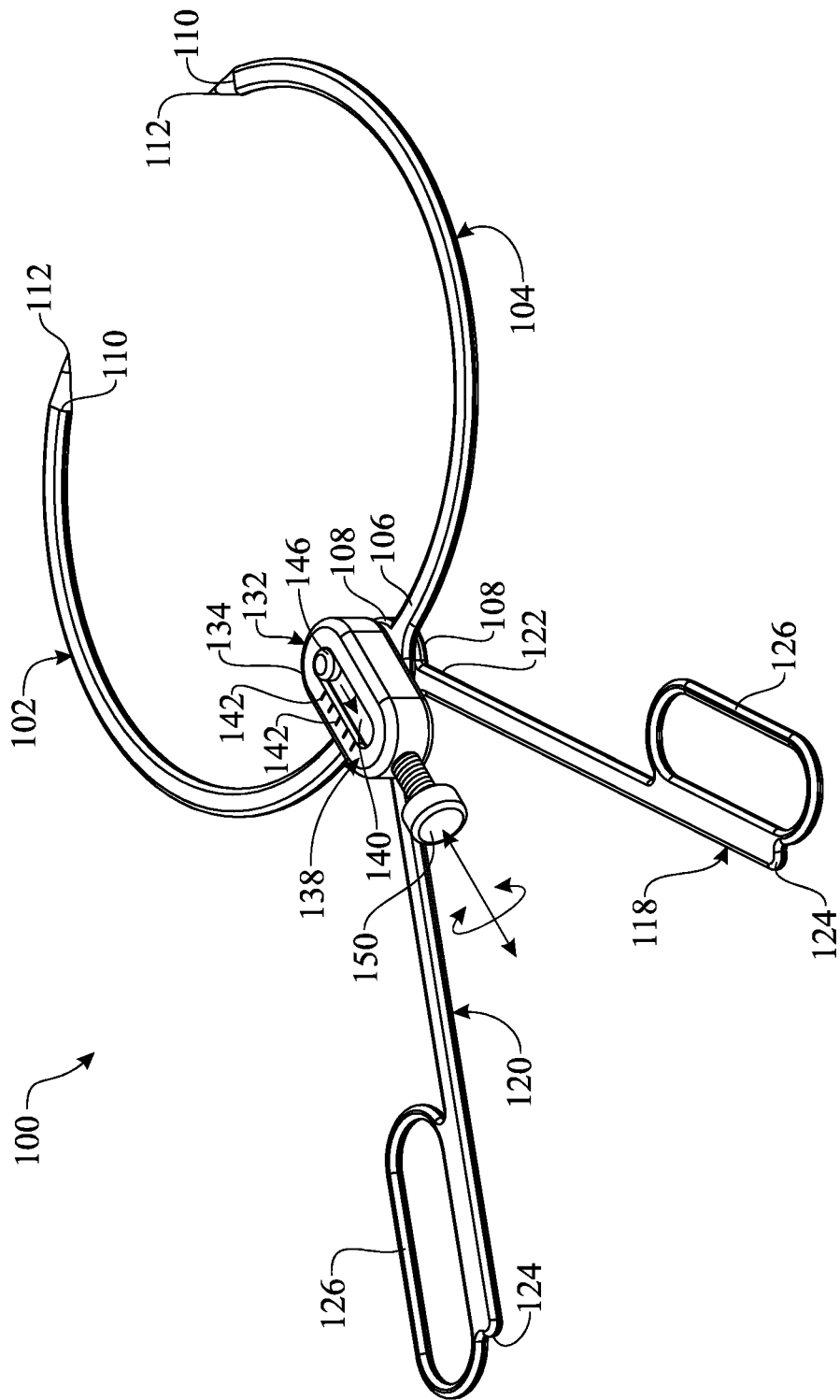
FIG. 1 presents a top perspective view showing a first embodiment of the force-limiting forceps of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward an axis aligning, force-limiting periarticular/intraarticular reduction forceps or clamp suitable for the reduction and realignment of specific anatomic structures.

Referring initially to FIGS. 1-5, a force-limiting forceps 100 is illustrated in accordance with a first illustrative embodiment of the present invention. As shown, the force-limiting forceps 100 may include a medial forceps tine 102 and a lateral forceps tine 104. Each of the medial forceps tine 102 and the lateral forceps tine 104 may be elongated and curved or generally semicircular with a proximal tine end 106 and a distal tine end 110. The distal tine end 110 may be tapered or pointed with a tine tip 112.

Figure 2:
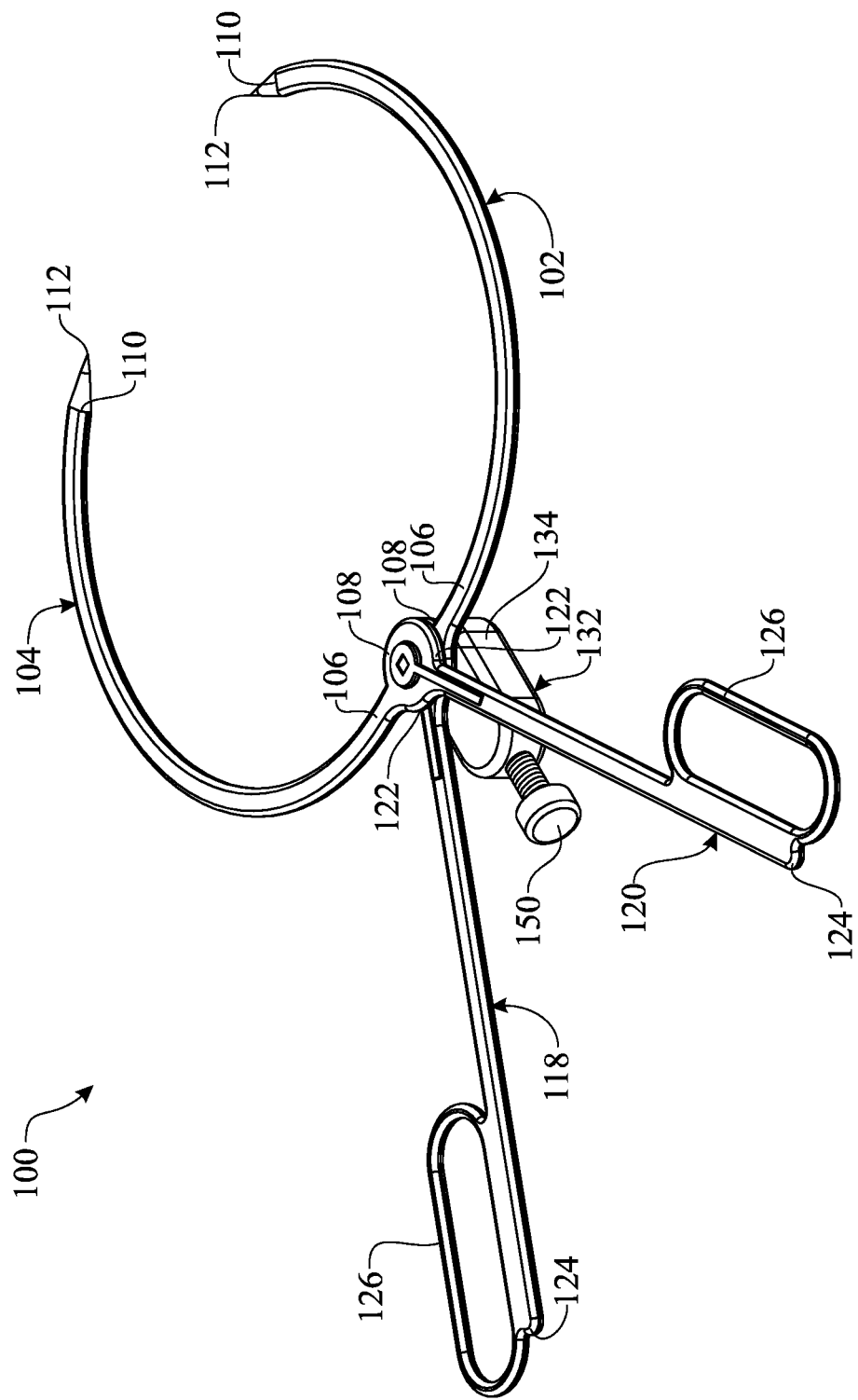
FIG. 2 presents a bottom perspective view of the first embodiment of the force-limiting forceps of the present invention.

As illustrated in FIG. 2, a tine/handle junction 108 may terminate the proximal tine end 106 of each of the medial forceps tine 102 and the lateral forceps tine 104. A lateral forceps handle 118 may extend from the tine/handle junction 108 of the medial forceps tine 102. A medial forceps handle 120 may extend from the tine/handle junction 108 of the lateral forceps tine 104. Each of the lateral forceps handle 118 and the medial forceps handle 120 may be generally elongated with a proximal handle end 122 and a distal handle end 124. As illustrated in FIG. 2, the proximal handle end 122 of the lateral forceps handle 118 may be attached to or fabricated in one piece with the tine/handle junction 108 of the medial forceps tine 102 according to the knowledge of those skilled in the art. In like manner, the proximal handle end 122 of the medial forceps handle 120 may be attached to or fabricated in one piece with the tine/handle junction 108 of the lateral forceps tine 104 according to the knowledge of those skilled in the art. In some embodiments, a finger loop 126 may be comprised in each of the lateral forceps handle 118 and the medial forceps handle 120 at the distal handle end 124 thereof. In some embodiments, the medial forceps tine 102, the lateral forceps handle 118 and the corresponding tine/handle junction 108 may be fabricated in one piece using molding, casting or other fabrication techniques known by those skilled in the art. Similarly, the lateral forceps tine 104, the medial forceps handle 120 and the corresponding tine/handle junction 108 may be fabricated in one piece.

A force quantifying and limiting mechanism 132 may engage the tine/handle junctions 108. The force quantifying and limiting mechanism 132 may be suitably adapted to limit the magnitude of clamping force which the lateral forceps handle 118 and the medial forceps handle 120 apply to the medial forceps tine 102 and the lateral forceps tine 104 according to the knowledge of those skilled in the art. In some embodiments, the force quantifying and limiting mechanism 132 may include a mechanism housing 134 which contains the functional components of the force quantifying and limiting mechanism 132.

As illustrated in FIG. 1, a force limiting selector 138 may be provided on the mechanism housing 134. The force limiting selector 138 may be suitably adapted to enable an operator (not illustrated) of the force-limiting forceps 100 to select the maximum magnitude or magnitude limit of the clamping force which the lateral forceps handle 118 and the medial forceps handle 120 apply to the medial forceps tine 102 and the lateral forceps tine 104. The force limiting selector 138 may include an elongated selector slot 140 in the mechanism housing 134. Spaced-apart force magnitude markings 142 may be provided on the mechanism housing 134 along the selector slot 140. A selector knob 146 may be slidably disposed in the selector slot 140. Accordingly, the selector knob 146 can be slid along the selector slot 140 to a selected force magnitude marking 142 to select the maximum magnitude or magnitude limit of the clamping force which the lateral forceps handle 118 and medial forceps handle 120 apply to the medial forceps tine 102 and the lateral forceps tine 104, irrespective of the gripping or clamping force which an operator (not illustrated) of the force-limiting forceps 100 applies to the lateral forceps handle 118 and the medial forceps handle 120. The force magnitude markings 142 may indicate graduated increments, in Newtons, of the magnitude of the clamping force which the lateral forceps handle 118 and medial forceps handle 120 apply to the medial forceps tine 102 and the lateral forceps tine 104. For example and without limitation, in some embodiments, the force magnitude markings 142 may include graduated increments in the amounts of 20 N, 40 N, 60 N, 80 N, 100 N, 120 N, 140 N, 160 N, 180 N, 200 N, 220 N, 240 N, 260 N, 280 N and 300 N, respectively.

In some embodiments, a threaded lock knob 150 may extend from the mechanism housing 134. The lock knob 150 may engage the functional components of the force quantifying and limiting mechanism 132 in such a manner as to lock the medial forceps tine 102 and the lateral forceps tine 104 in place at a desired or selected clamping force according to the knowledge of those skilled in the art.

Figure 3:
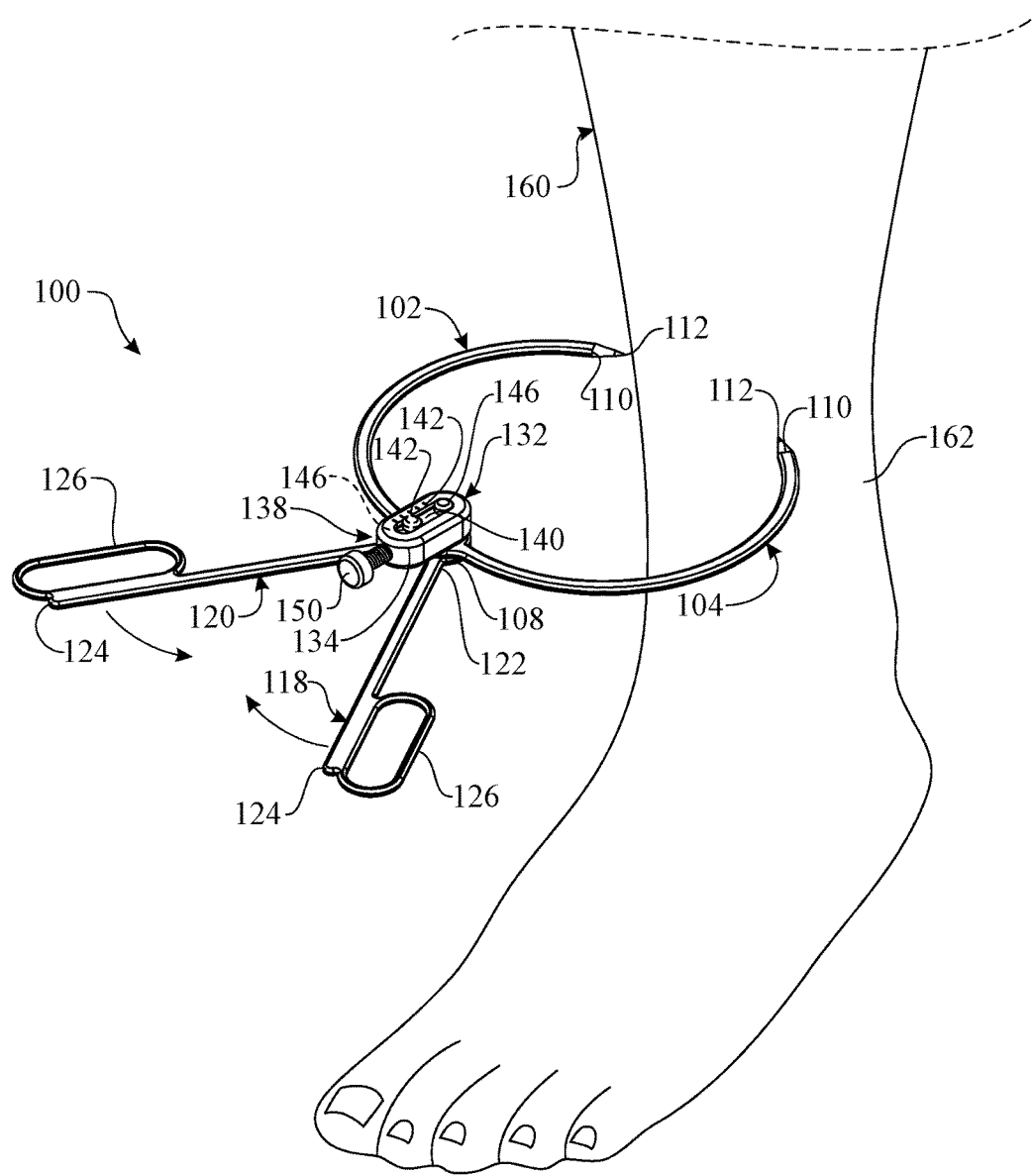
FIG. 3 presents a top perspective view of the first embodiment of the force-limiting forceps of the present invention preparatory to application of the forceps on a patient's leg.
Figure 4:
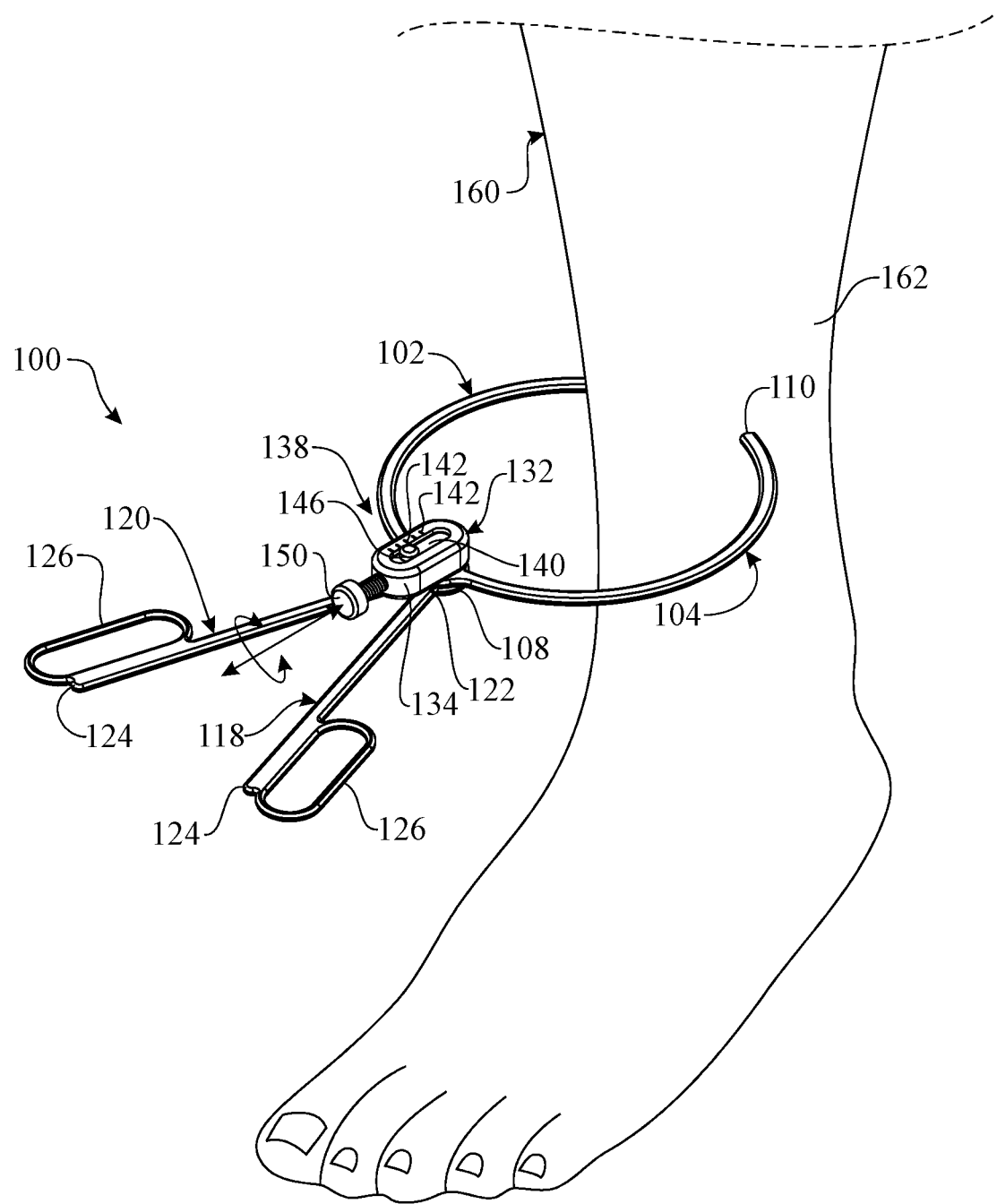
FIG. 4 presents a top perspective view of the force-limiting forceps illustrated in FIG. 3, applied to the patient's leg, more particularly illustrating actuation of a lock knob to secure the forceps tines at a selected limited magnitude of the clamping force.
Figure 5:
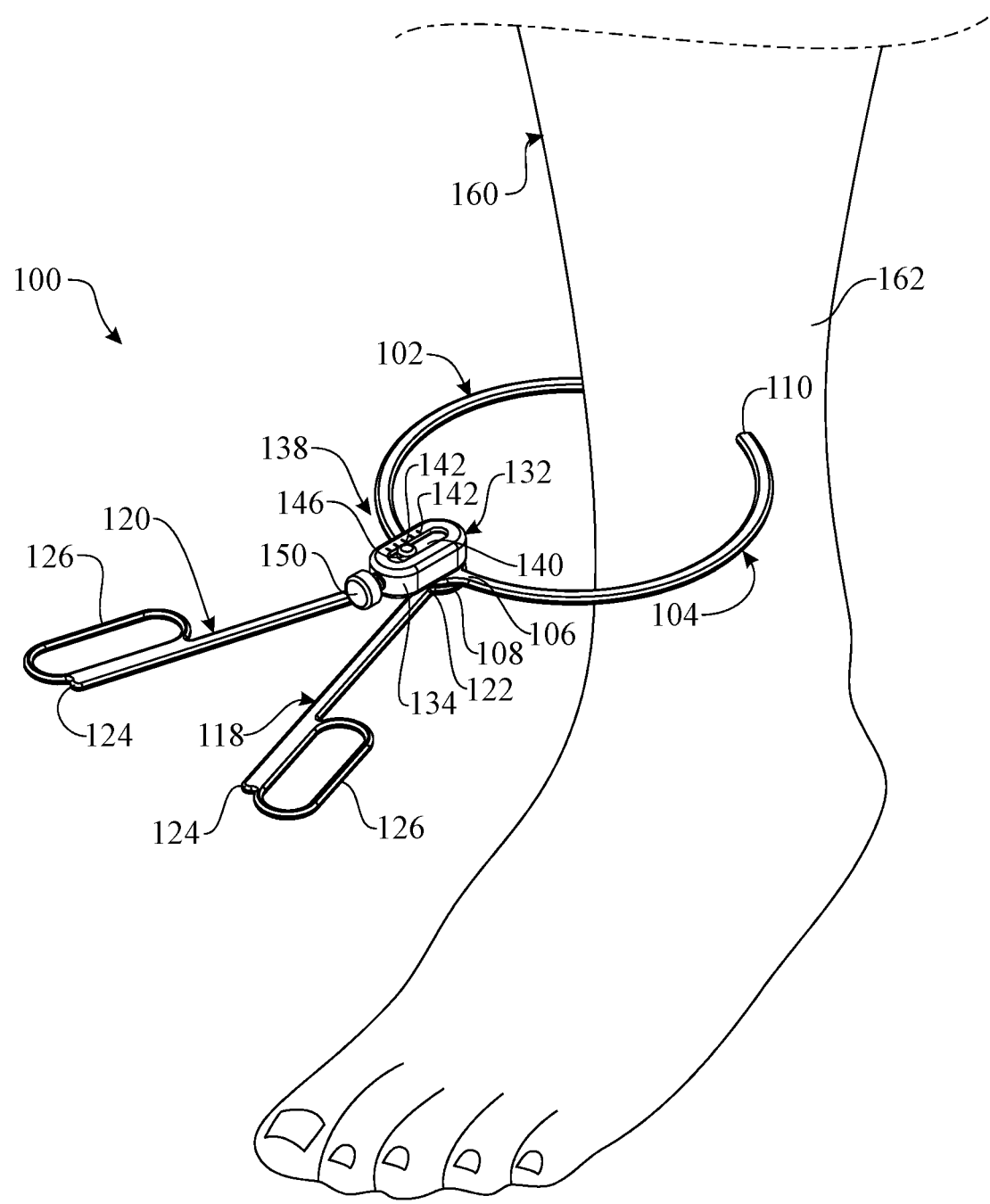
FIG. 5 presents a top perspective view of the force-limiting forceps illustrated in FIG. 3, with the lock knob secured.

As illustrated in FIGS. 3-5, in typical application, the force-limiting forceps 100 may be used in the periarticular/intraarticular reduction of anatomical structures such as in the repairing of injuries to the distal tibiofibular syndesmosis in a leg 162 of a patient 160. Accordingly, as illustrated in FIG. 3, the medial forceps tine 102 and the lateral forceps tine 104 may initially be opened, typically by separation of the lateral forceps handle 118 and the medial forceps handle 120, to facilitate placement of the medial forceps tine 102 and lateral forceps tine 104 on respective sides of the patient's leg 162. The force limiting selector 138 may be engaged to enable a surgeon or other operator (not illustrated) of the force-limiting forceps 100 to select the maximum magnitude or magnitude limit of the clamping force which the lateral forceps handle 118 and the medial forceps handle 120 apply to the medial forceps tine 102 and the lateral forceps tine 104 as the medial forceps tine 102 and the lateral forceps tine 104 apply the clamping force to the distal tibiofibular syndesmosis. To this end, the selector knob 146 may be slid along the selector slot 140 until the selector knob 146 aligns or registers with the force magnitude marking 142 which corresponds to the desired maximum magnitude or magnitude limit of the clamping force which the lateral forceps handle 118 and medial forceps handle 120 will apply to the medial forceps tine 102 and the lateral forceps tine 104 irrespective of the squeezing or clamping force which the operator applies to the lateral forceps handle 118 and medial forceps handle 120. The operator may then grasp and squeeze the lateral forceps handle 118 and the medial forceps handle 120 toward each other, as illustrated in FIG. 3, such that the tine tips 112 on the respective medial forceps tine 102 and lateral forceps tine 104 engage the distal tibiofibular syndesmosis in the patient's leg 162, as illustrated in FIGS. 4 and 5. The force limiting selector 138 limits the magnitude of the clamping force which the medial forceps tine 102 and lateral forceps tine 104 apply to the distal tibiofibular syndesmosis irrespective of the squeezing or clamping force which the operator applies to the lateral forceps handle 118 and medial forceps handle 120. Thus, the operator of the force-limiting forceps 100 may fully engage the lateral forceps handle 118 and the medial forceps handle 120 without risking over-compression of the distal tibiofibular syndesmosis or other anatomical structure to which the medial forceps tine 102 and the lateral forceps tine 104 are applied. This expedient may reduce the incidence of iatrogenic syndesmotic coronal plane malreduction. In some applications, the lock knob 150 may be actuated to lock the medial forceps tine 102 and the lateral forceps tine 104 in place at a desired or selected clamping force such that formal reduction of the anatomical structure can proceed using other devices (not illustrated).

Figure 6:
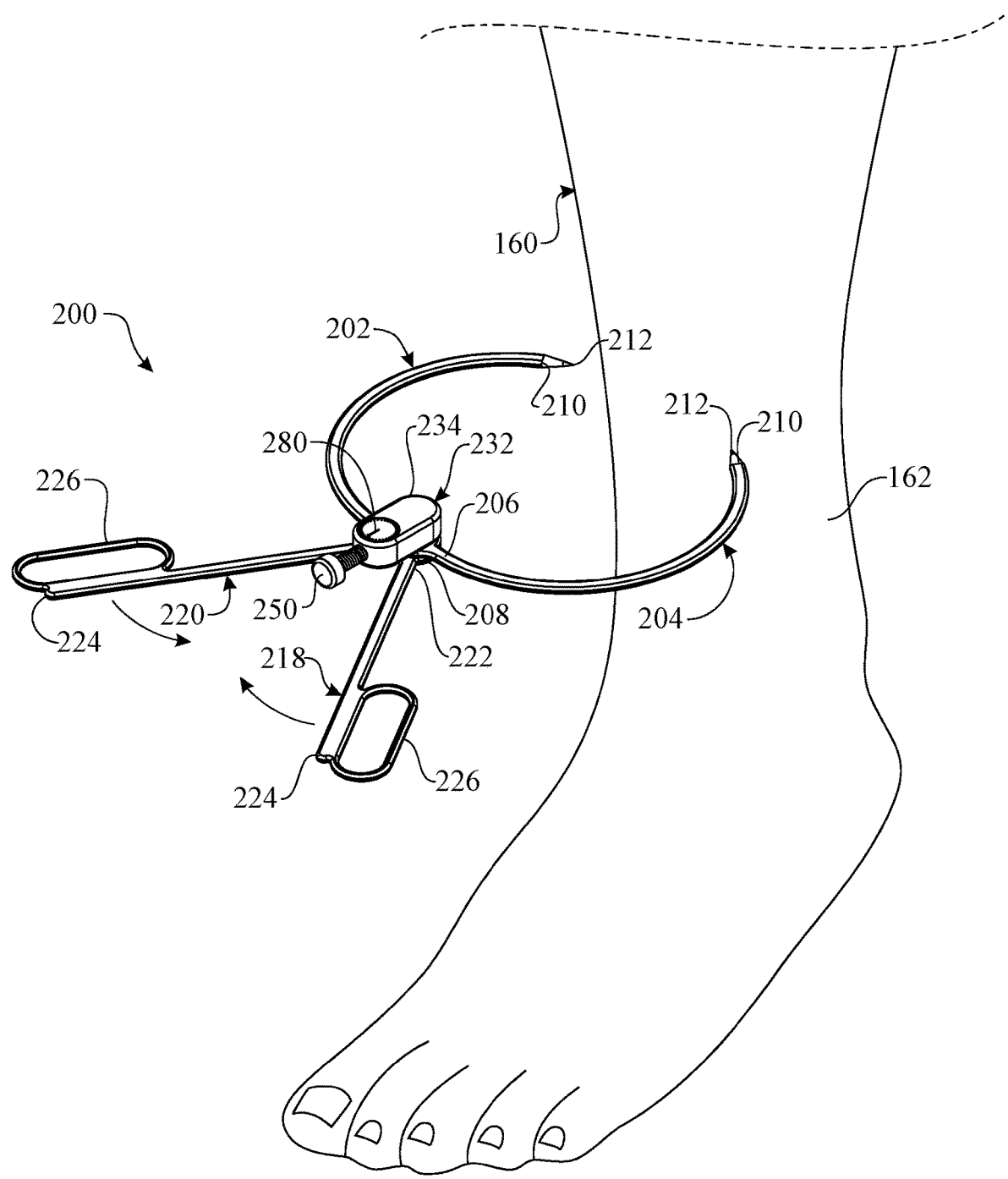
FIG. 6 presents an exploded top perspective view of a second embodiment of the force-limiting forceps of the present invention preparatory to application of the forceps tines on a patient's leg.
Figure 7:
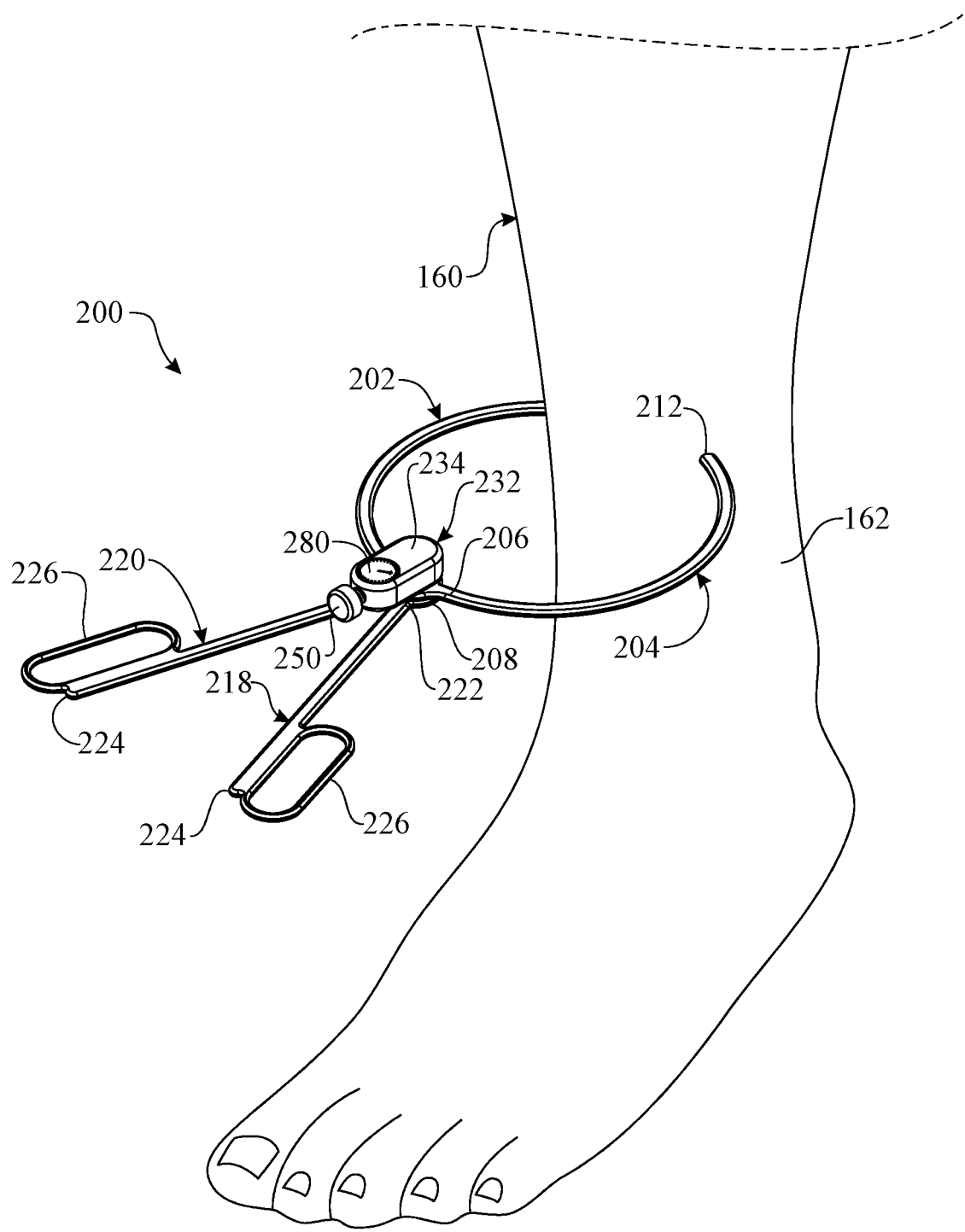
FIG. 7 presents a top perspective view of the second embodiment of the force-limiting forceps of the present invention with the forceps tines applied on the patient's leg and including a force indicating gauge which indicates a magnitude of the clamping force which the forceps tines apply to the anatomical structure.

Referring next to FIGS. 6 and 7, a force-limiting forceps 200 in accordance with a second illustrative embodiment of the present invention is shown preparatory to application of the medial forceps tine 202 and the lateral forceps tine 204 on a patient's leg 162 in FIG. 6. In the force-limiting forceps 200, elements which are analogous to the respective elements of the force-limiting forceps 100 that was heretofore described with respect to FIGS. 1-5 are designated by the same respective numerals in the 200-299 series in FIGS. 6 and 7. Application of the force-limiting forceps 200 may be as was heretofore described with respect to the force-limiting forceps 100 in FIGS. 1-5. Similarly to the previous embodiment, a mechanism housing 234 may contain a force-limiting mechanism which limits the clamping force which the lateral forceps handle 218 and medial forceps handle 220 will apply to the medial forceps tine 202 and the lateral forceps tine 204 to a desired value, irrespective of the squeezing or clamping force which the operator applies to the lateral forceps handle 218 and medial forceps handle 220.

In the present embodiment, a force indicating gauge 280 may be provided on the mechanism housing 234 of the force quantifying and limiting mechanism 232. The force indicating gauge 280 may be suitably adapted to quantify and indicate the magnitude of the clamping force which the medial forceps tine 202 and the lateral forceps tine 204 apply to the anatomical structure according to the knowledge of those skilled in the art. In some embodiments, the force indicating gauge 280 may be a dial gauge, as illustrated. In other embodiments, the force indicating gauge 280 may be any other type of gauge which is capable of measuring or quantifying and indicating or displaying the magnitude of the clamping force. In some embodiments, the lock knob 250 may be actuated to lock the medial forceps tine 202 and the lateral forceps tine 204 in place at the clamping force which is indicated by the force indicating gauge 280.

Figure 8:
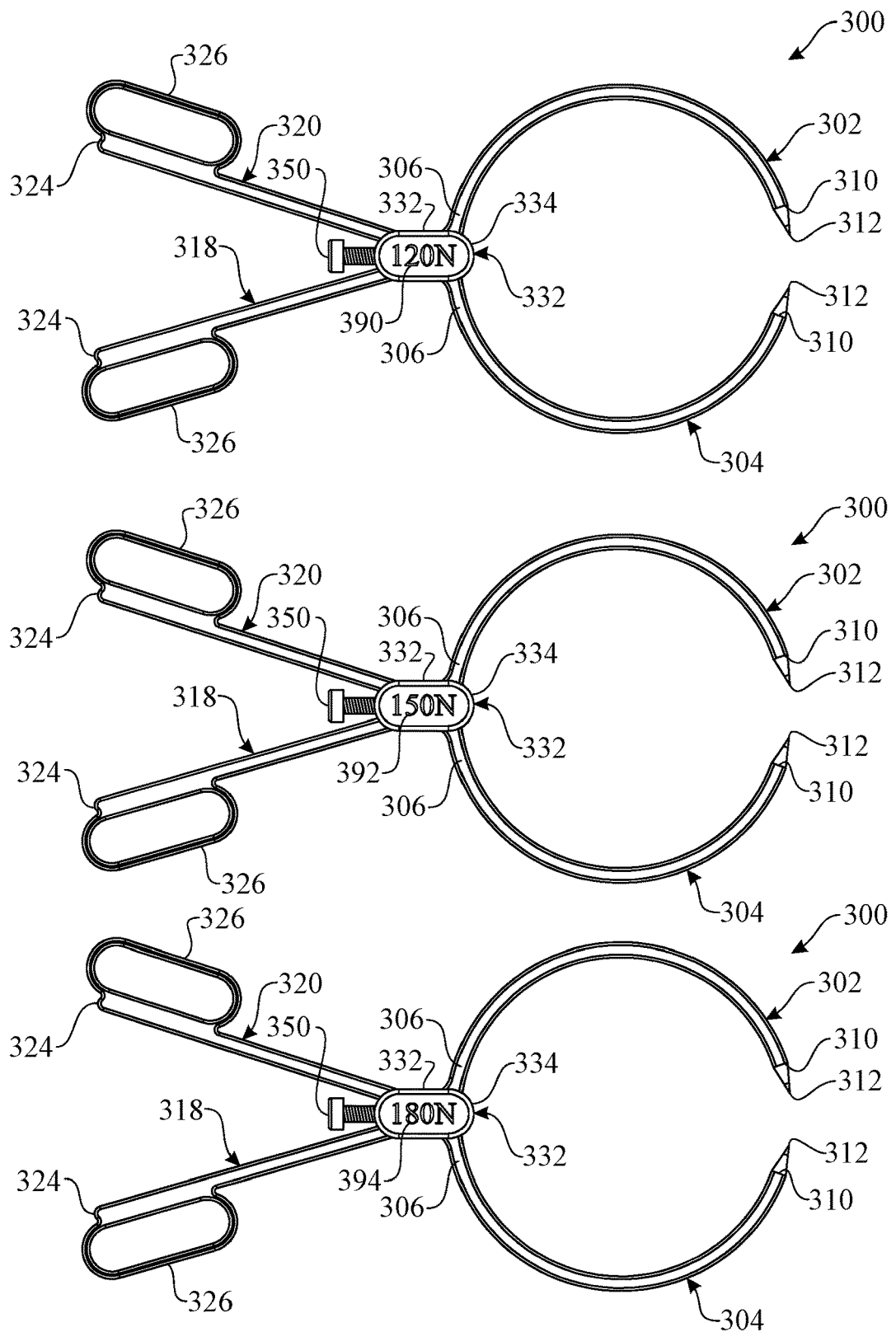
FIG. 8 presents a top view of three alternative force-limiting forceps in accordance with a third embodiment of the present invention.

Referring next to FIG. 8, a top perspective view of three variations of a force-limiting forceps 300 in accordance with a third illustrative embodiment of the present invention is shown. In the force-limiting forceps 300, elements which are analogous to the respective elements of the force-limiting forceps 100 that was heretofore described with respect to FIGS. 1-5 are designated by the same respective numerals in the 300-399 series in FIG. 8. Application of the force-limiting forceps 300 may be as was heretofore described with respect to the force-limiting forceps 100 in FIGS. 1-5. In the present embodiment, the maximum force to be applied by the forceps is not adjustable. Instead, the force quantifying and limiting mechanism 332 limits the clamping force which the lateral forceps handle 318 and the medial forceps handle 320 apply to the medial forceps tine 302 and the lateral forceps tine 304 to a predefined, fixed magnitude. Force indicating indicia 390, 392, 394 may be provided on the mechanism housing 334 of the force quantifying and limiting mechanism 332. The force indicating indicia 390, 392, 394 may indicate the predefined, fixed magnitude of the maximum clamping force which the lateral forceps handle 318 and the medial forceps handle 320 apply to the medial forceps tine 302 and the lateral forceps tine 304. For example and without limitation, the force indicating indicia 390 in the uppermost forceps of FIG. 8 may indicate a maximum clamping force having a predefined, fixed magnitude of 120 N. The force indicating indicia 392 in the middle embodiment of FIG. 8 may indicate a maximum clamping force having a predefined, fixed magnitude of 150 N. The force indicating indicia 394 in the bottommost embodiment of FIG. 8 may indicate a maximum clamping force having a predefined, fixed magnitude of 180 N. Thus, these respective embodiments of the force-limiting forceps 300 come non-adjustably preset to limit the magnitude of the clamping force of the medial forceps tine 302 and lateral forceps tine 304 at 120 N, 150 N and 180 N, respectively. It will be recognized and understood that these limited clamping force magnitudes are exemplary and that the force-limiting forceps 300 may be configured to limit the clamping force to other maximum magnitudes in different embodiments.

It will be appreciated by those skilled in the art that results which are attained by the axis aligning, force-limiting forceps of the present invention are innovative. The application of a limited or quantified clamping force which is embodied in the function of the force-limiting forceps as heretofore described will improve on the current standard of care for ORIF of ankle fractures with syndesmotic disruption and/or isolated syndesmotic disruption. The axis aligning, force-limiting forceps may directly decrease iatrogenic sagittal, axial, and coronal plane syndesmotic malreduction rates by surgeons, restoring the ankle joint's contact area/forces/pressures and improving functional outcomes while mitigating the incidence of post traumatic osteoarthrosis of the ankle, which has been shown to be as disabling as hip and knee arthrosis with respect to patients' quality of life.

Conventional forceps used in the reduction and realignment of anatomic structures are not designed to address the problem which is addressed by the axis aligning, force-limiting forceps of the present invention. Moreover, conventional forceps are not adequately amenable to application to the distal tibiofibular syndesmosis. The tines of some conventional forceps are not suitably shaped, sized or oriented for precise reduction of two osseous long bones, nor could they be easily applied to important anatomic landmarks of the fibula/tibia by the surgeon intraoperatively. Placement of the tines of the forceps intraoperatively is absolutely critical, as is subsequent fixation device trajectory along the desired axis. The axis aligning, force-limiting forceps of the present disclosure allows exact placement of the lateral tine on the lateral peroneal/malleolar ridge of the fibula, as well as the medial tine's placement on the tibia fluoroscopically, at the discretion of the surgeon. The screw's trajectory is easily aligned as described below, preventing off-axis, eccentric reduction forceps placement and sub-optimal fixation trajectories which cause iatrogenic sagittal plane malreduction, with secondary axial/coronal plane malreduction as well. Not only does the axis aligning, force-limiting forceps of the present invention address this problem, but the axis aligning, force-limiting forceps itself differs in design (axis aligning targets, low profile tines) to allow for clear, and easy visualization of the transmalleolar/centroidal axis with internal rotation of the operative limb, allowing surgeons to consistently and reliably place fixation devices accurately to maintain the realigned structures (fibula, tibia, syndesmosis), without the traditional subjectivity that has historically resulted in high malreduction rates. This technology may result in improved reduction in the coronal/sagittal/axial planes, restoring TTJ contact area/forces/pressures and improving patient outcomes.

Referring next to FIGS. 9-18, a force-limiting forceps 400 in accordance with a fourth illustrative embodiment of the present invention is shown. In the force-limiting forceps 400, elements which are analogous to the respective elements of the force-limiting forceps 100 that was heretofore described with respect to FIGS. 1-5 are designated by the same respective numerals in the 400-499 series in FIGS. 9-18.

Figure 9:
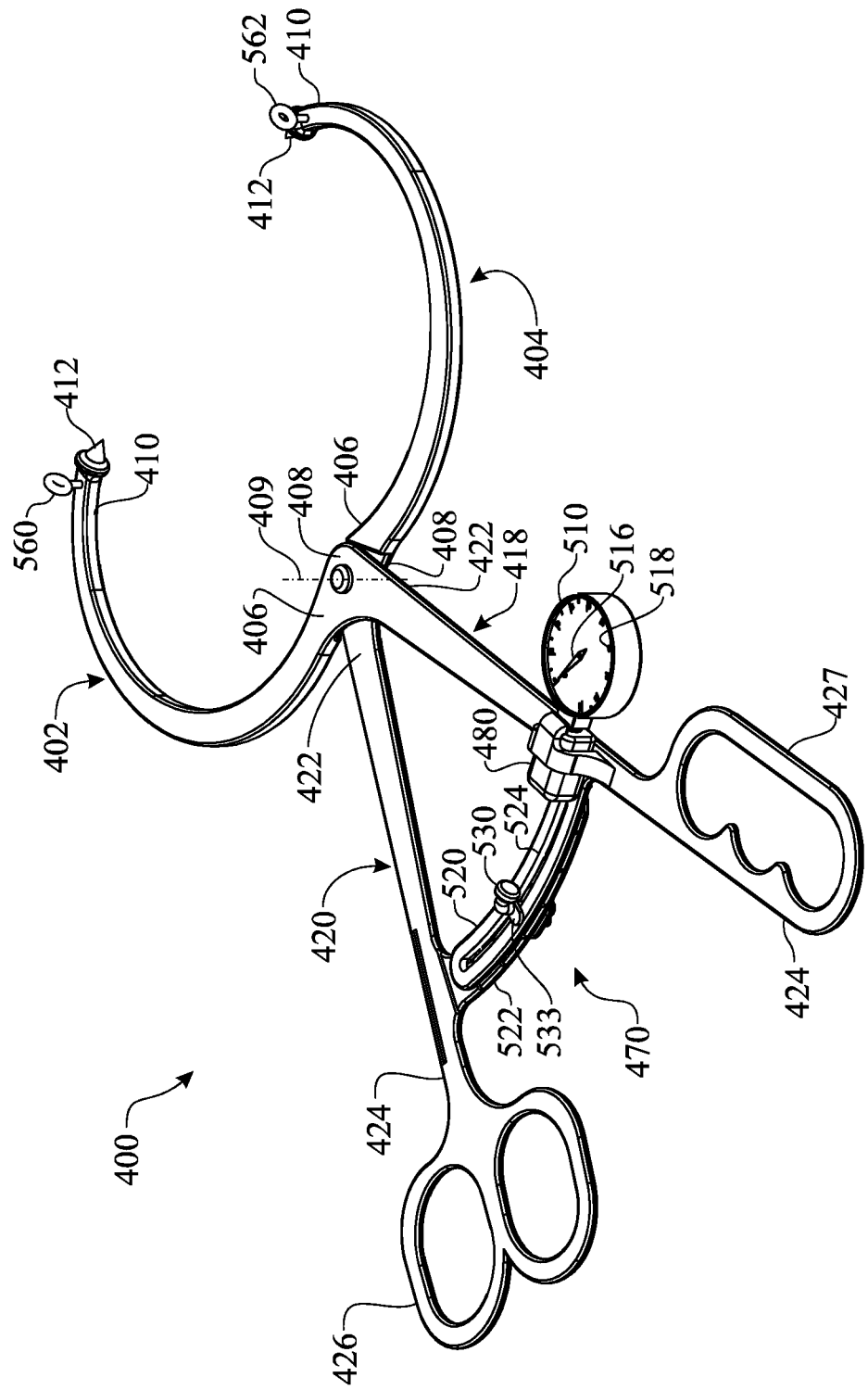
FIG. 9 presents a top perspective view showing a fourth embodiment of the force-limiting forceps of the present invention.

Referring initially to FIG. 9, similarly to the previous embodiments, the force-limiting forceps 400 comprises a medial forceps tine 402 and a lateral forceps tine 404, each having a proximal tine end 406 and a distal tine end 410. The distal tine end 410 may be tapered or pointed with a tine tip 412. A tine/handle junction 408 may terminate the proximal tine end 406 of each of the medial forceps tine 402 and the lateral forceps tine 404. A lateral forceps handle 418 may extend from the tine/handle junction 408 of the medial forceps tine 402. A medial forceps handle 420 may extend from the tine/handle junction 408 of the lateral forceps tine 404. A dual-finger loop 426 and a triple-finger loop 427 may be comprised in the lateral forceps handle 418 and the medial forceps handle 420, respectively; however, alternative finger loops or other handle shapes are contemplated without departing from the scope of the present disclosure. The medial forceps tine 402 and lateral forceps handle 418 form a first unit, while the lateral forces tine 404 and medial forceps handle 420 form a second unit, wherein these units are pivotably connected to one another at the tine/handle junctions 408 and are pivotable relative to one another about a rotation axis 409.

Similarly to previous embodiments, the force-limiting forceps 400 of the present embodiment comprises a force quantifying and limiting mechanism 470. As will be described in greater detail hereinafter, the force quantifying and limiting mechanism 470 allows measuring the force applied by the force-limiting forceps 400, indicating the applied force to the user, and locking the force-limiting forceps 400 in a specific position (i.e. exerting a specific force) in order to prevent forces higher than said specific force from being applied.

Figure 16:
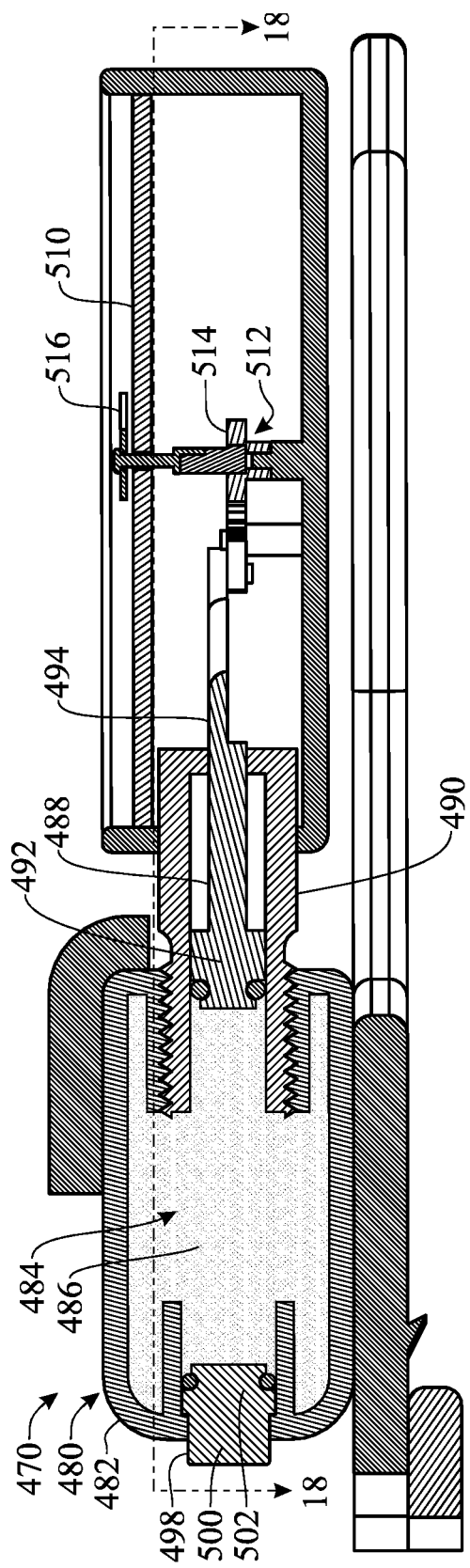
FIG. 16 presents a cross-sectional side elevation view of the mechanical pressure gauge, gear assembly and dial, taken along section plane 16-16 indicated in FIG. 10.
Figure 17:
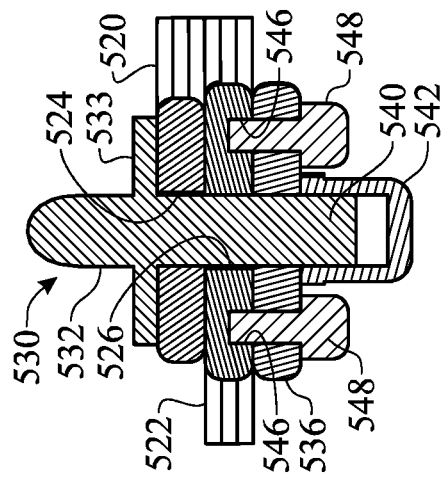
FIG. 17 presents a cross-sectional side elevation view of the pusher and first and second arc-shaped arms, taken along section plane 17-17 indicated in FIG. 10.
Figure 18:
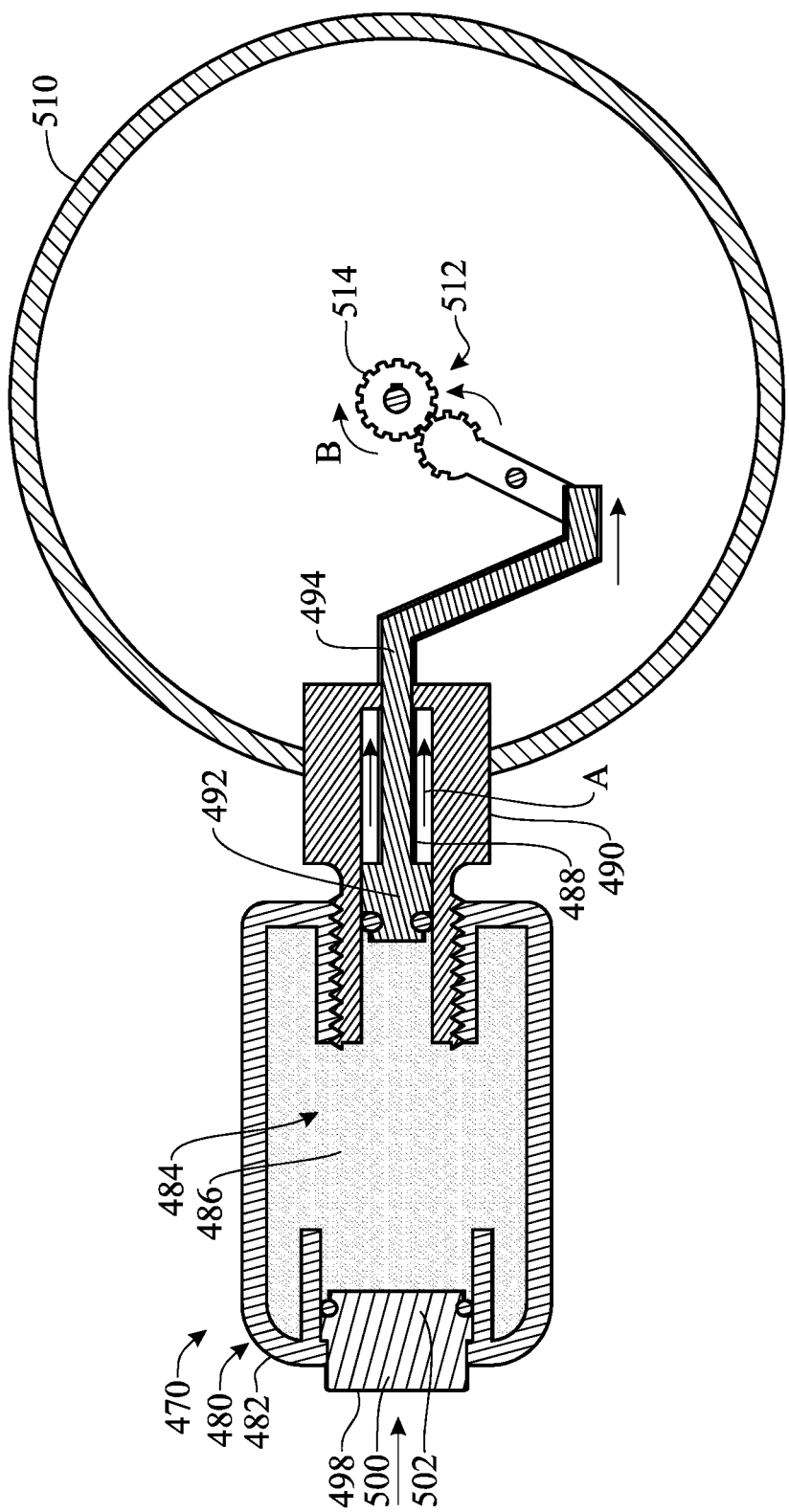
FIG. 18 presents a top plan view of the mechanical pressure gauge, gear assembly and dial, taken along section plane 18-18 indicated in FIG. 16.

The force quantifying and limiting mechanism 470 of the present embodiment comprises a mechanical pressure gauge 480, shown in greater detail in FIGS. 16 and 18. The mechanical pressure gauge 480 comprises a hollow container or housing 482 having an internal fluid chamber 484 containing a fluid 486 such as, but not limited to, oil. A piston 488 is movably arranged within a piston-receiving portion or neck 490 comprised in the housing 482. The piston 488 comprises a piston head 492 and a piston shaft 494. The piston head 492 seals and moves along internal walls of the piston-receiving neck 490, and is in contact with the fluid 486 housed inside the housing 482. In turn, the piston shaft 494 extends from the piston head 492 and protrudes outwardly from the housing 482 at an end of the piston-receiving neck 490.

As further shown in FIGS. 16 and 18, on a different side of the housing 482, a movable button 498 is provided, with a first portion 500 of the button 498 extending out of the housing 482 and a second portion 502 of the button 498 arranged within the internal fluid chamber 484 and in contact with the fluid 486.

As shown in FIG. 9, the force quantifying and limiting mechanism 470 of the present embodiment further includes a dial 510 configured to provide a visual indication of the pressure applied by the medial forceps tine 402 and lateral forceps tine 404. As shown in FIGS. 16 and 18, the dial 510 comprises an internal gear assembly 512, best shown in FIG. 18, which cooperates with the piston shaft 494 such that a rectilinear movement of the piston shaft 494, indicated in FIG. 18 by arrows A, is converted into a rotational movement of a gear 514, indicated in FIG. 18 by arrow B. The gear 514, in turn, is configured to rotate jointly with a pointer 516 of the dial 510. The dial 510 further comprises angularly-spaced-apart visual markings 518 to provide a visual reading of the mechanical pressure applied by the medial forceps tine 402 and lateral forceps tine 404 corresponding to the different rotational positions of the pointer 516 resulting from the movement of the piston 488, as will be described in greater detail hereinafter.

Turning again to FIG. 9, the force quantifying and limiting mechanism 470 further includes a pusher 530, which is movably arranged between the lateral forceps handle 418 and the medial forceps handle 420. The pusher 530 is carried by a first arm 520 and a second arm 522 which are comprised in, and preferably integrally-formed with, the lateral forceps handle 418 and the medial forceps handle 420, respectively. The first and second arms 520 and 522 are arc-shaped, extend towards one another, and overlap with one another, as shown. An elongated, arc-shaped first slot 524 is formed along the first arm 520. Similarly, as best shown in the enlarged bottom view of FIG. 12, an elongated, arc-shaped second slot 526 is formed along the second arm 522. The first and second slots 524 and 526 are disposed overlapping with one another, as shown, to jointly form a channel.

The mechanical pressure gauge 480 is carried by one of the handles, while the pusher 530 is carried by the other handle. For instance, in the present embodiment, the mechanical pressure gauge 480 is carried by, and rotates jointly with, the lateral forceps handle 418, while the pusher 530 is carried by, and rotates jointly with, the medial forceps handle 420. Thus, when the lateral and medial forceps handles 418 and 420 are pivoted towards or away one another about the rotation axis 409, the mechanical pressure gauge 480 and pusher 530 are consequently moved towards or away from another, respectively, as shown for instance in FIGS. 10 and 11.

Figure 12:
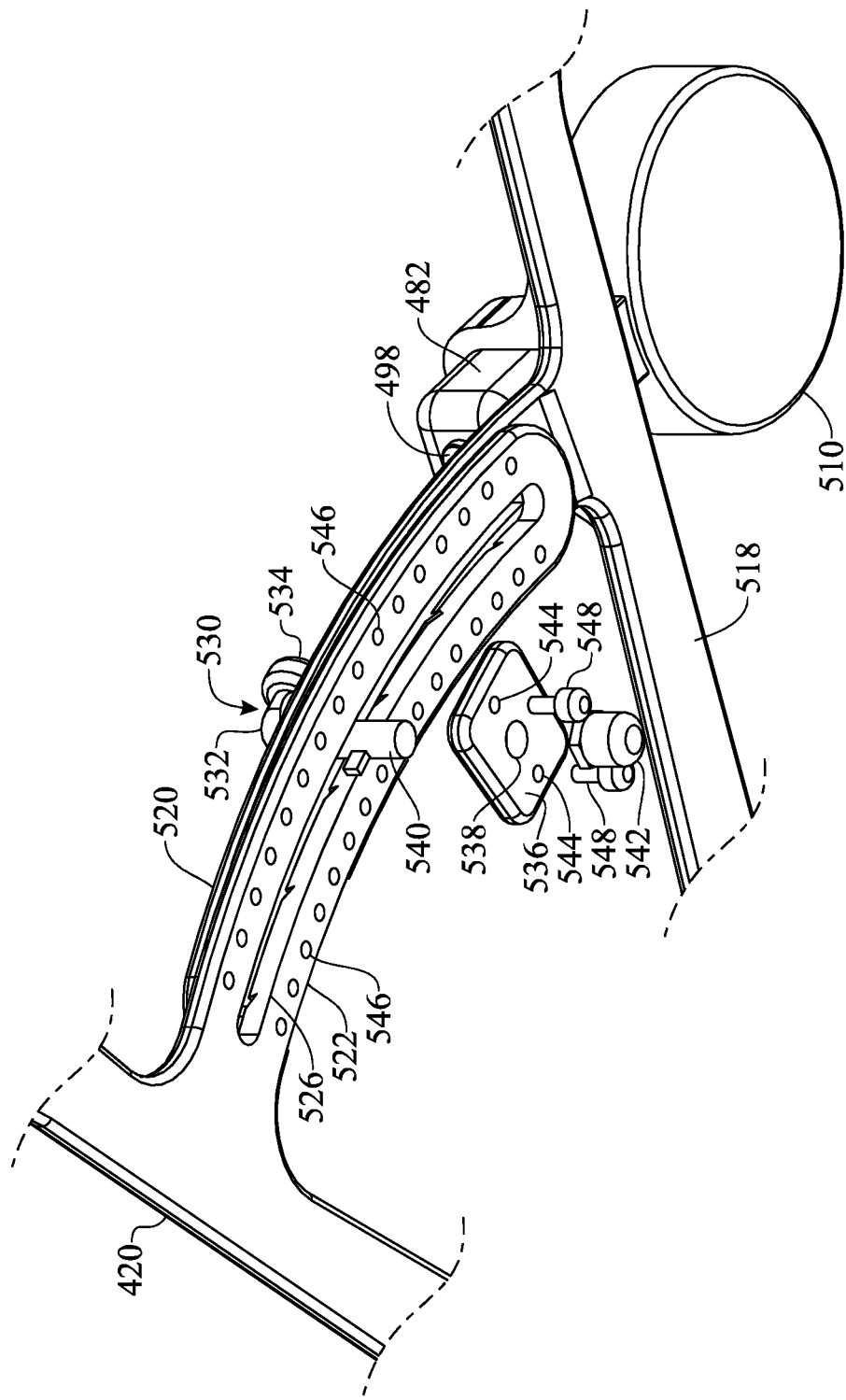
FIG. 12 presents an enlarged, exploded bottom perspective view of the force quantifying and limiting mechanism, more particularly showing details of the pusher and aligned slots.
Figure 13:
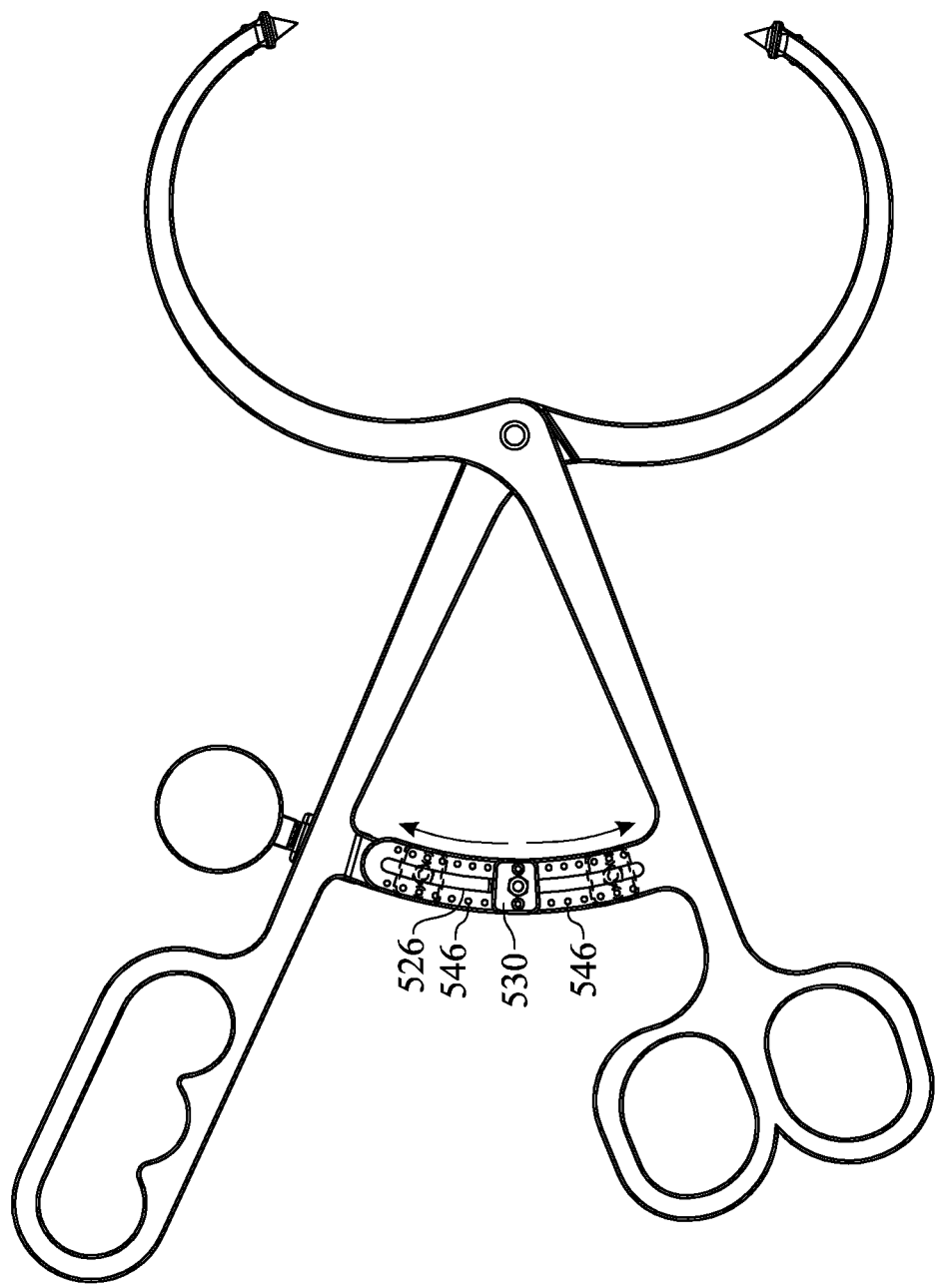
FIG. 13 presents a bottom plan view of the force-limiting forceps of FIG. 9, illustrating movement of the pusher along the overlapping slots of the overlapping arc-shaped arms.

Details of the pusher 530 can be seen in the bottom views of FIGS. 12 and 13. As shown, the pusher 530 comprises a pusher body 532 that extends through the channel formed by the overlapping first and second slots 524 and 526. On a top side thereof, the pusher body 532 comprises a shoulder portion 533 configured to rest on the first arm 520, as best shown in FIG. 18. As shown in FIG. 12, a pusher end 534 of the pusher body 532 is located on one side of the overlapping first and second arms 520 and 522, and an attachment plate 536 is arranged on an opposite, second side of the overlapping first and second arms 520 and 522. The attachment plate 536 includes a first opening 538 for the fitting therethrough of a threaded end 540 of the pusher body 532. A nut 542 threads onto the threaded end 540 of the pusher body 532 in order to retain the attachment plate 536 in place against the second arm 522. The attachment plate 536 further comprises two additional openings 544 configured to selectively align with a series of openings 546 formed in angularly-spaced-apart, discrete positions along the second arm 522. Two fasteners 548 are shaped and sized to extend through the openings 544 in the attachment plate 536 and thread into the openings 546 of the second arm 522, as also shown in FIG. 18, in order to lock the pusher body 532 and attachment plate 536 in a fixed position relative to the second arm 522 so that the pusher body 532 rotates jointly with the second arm 522 about the rotation axis 409. By unfastening the fasteners 548 and readjusting them to connect with different openings 546 in the second arm 522, the user can adjust the separation or angular distance between the pusher end 534 of the pusher 530 and the button 498 of the pressure gauge 480 in order to adjust the force-limiting forceps 400 to differently sized tissues that are to be clamped. In turn, sufficient tightening of the nut 542 allows to frictionally prevent the overlapping first and second arms 520 and 522 from moving relative to one another by compressing the first and second arms 520 and 522 in between the shoulder portion 533 of the pusher body 532 and the attachment plate 536, thus preventing rotation of the lateral and medial forceps handles 418 and 420 relative to one another about the rotation axis 409; sufficient loosening of the nut 542, on the other hand, frees the lateral and medial forceps handles 418 and 420 to move relative to one another about the rotation axis 409.

Figure 10:
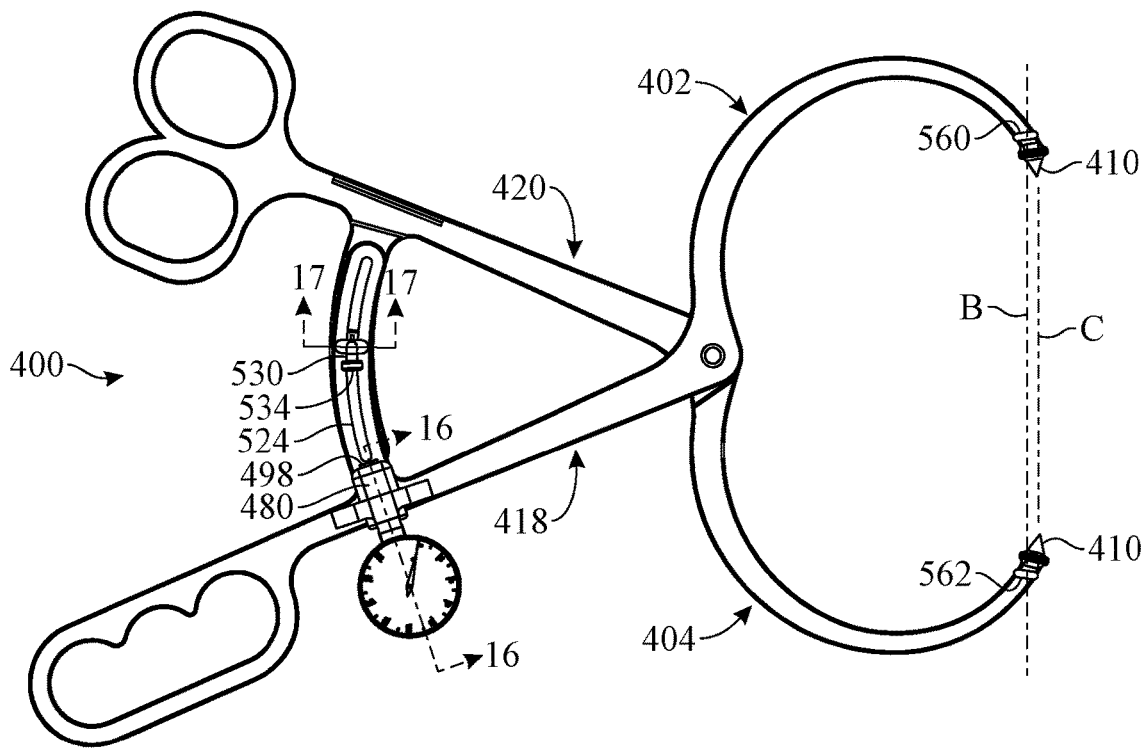
FIG. 10 presents a top plan view of the force-limiting forceps of FIG. 9, which the pusher shown angularly spaced apart from the mechanical pressure gauge.
Figure 11:
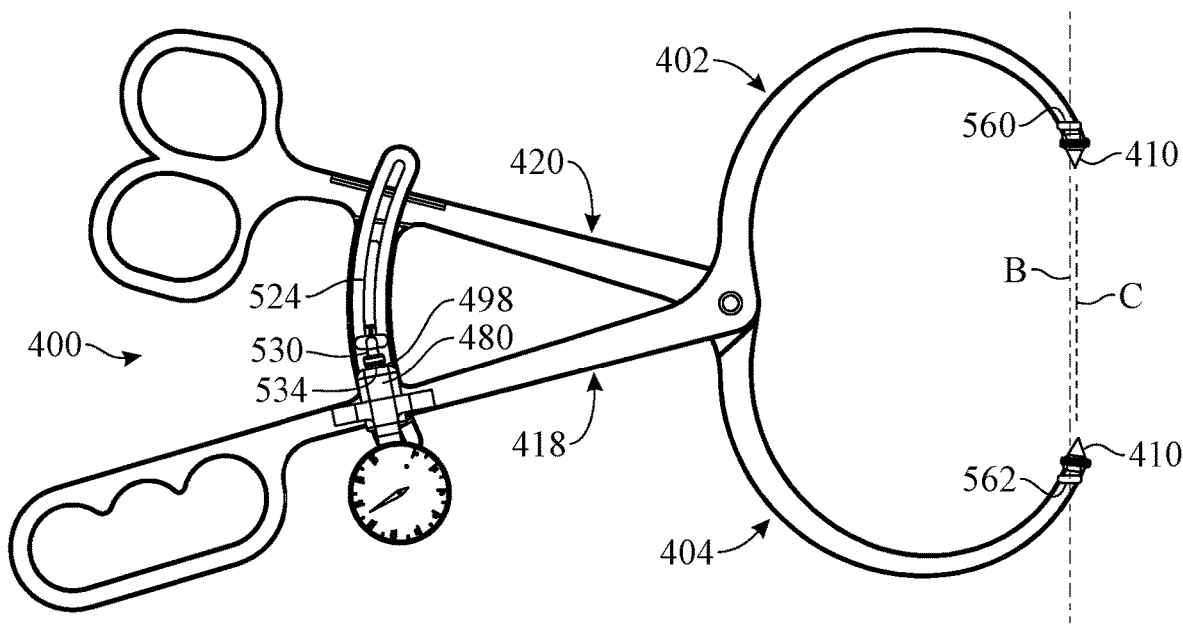
FIG. 11 presents a top plan view of the force-limiting forceps of FIG. 9, which the pusher shown pressing a button on the mechanical pressure gauge and the dial showing a visual indication of the force being applied by the lateral and medial forceps tines.
Figure 15:
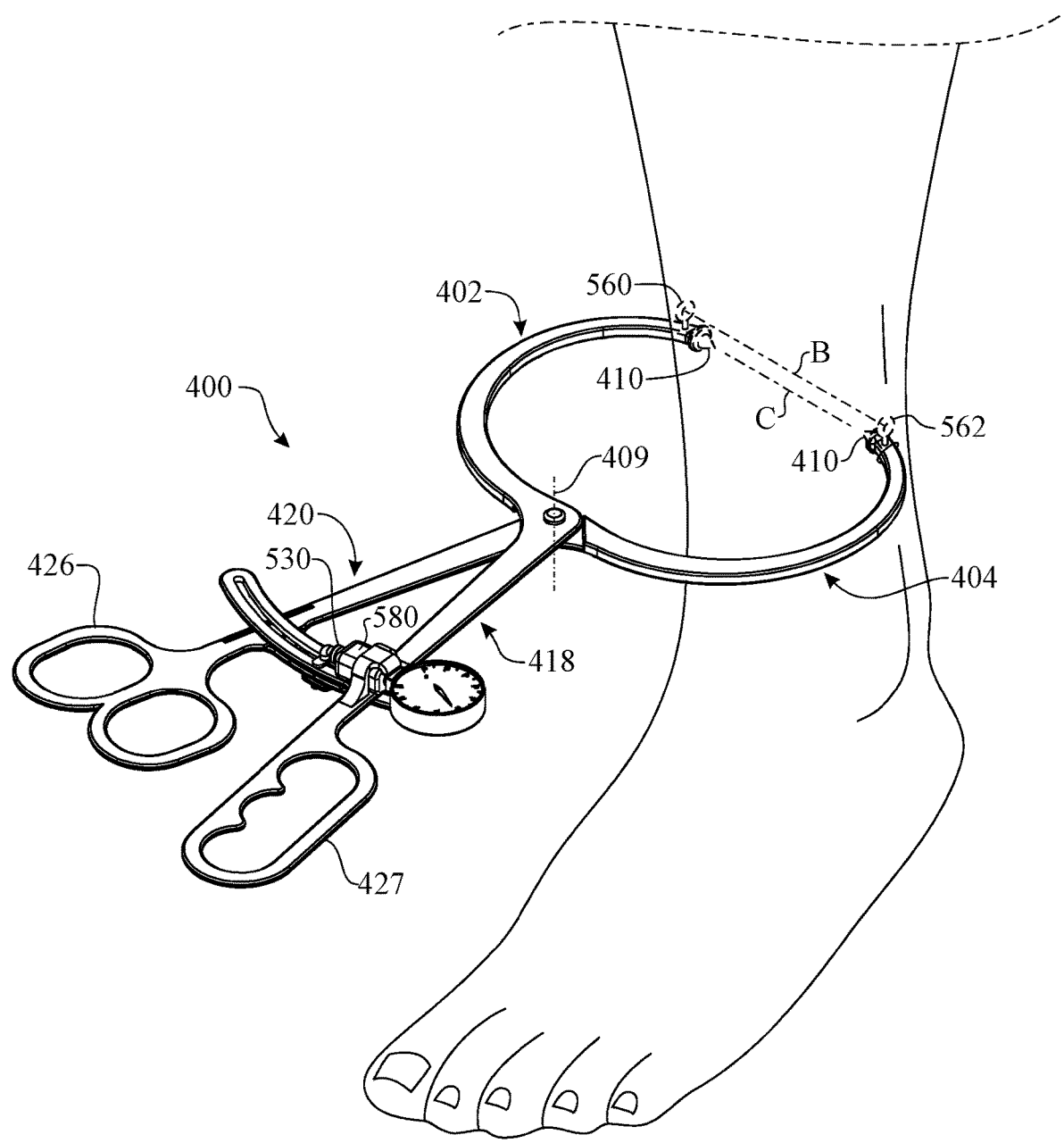
FIG. 15 presents a second step of an illustrative method of operation of the force-limiting forceps of FIG. 9.

Referring back to FIG. 9, the force-limiting forceps 400 of the present embodiment further comprises respective targets 560, 562 at the distal tine ends 410 of the medial and lateral forceps tines 402 and 404. The targets 560, 562 are made of a material or materials which is/are visible under X-ray imaging (e.g., fluoroscopy). The targets 560, 562 are arranged in a same orientation, i.e. facing one another and configured to align in a direction B which is parallel to the direction C in which the tine tips 412 align with one another, as best shown in FIGS. 10, 11 and 15. In some embodiments, the targets 560, 562 may be individually and reversibly removed (e.g., unscrewed) from the tine if so desired. Alternatively or additionally, the height of each target 560, 562 may be adjustable, such as by adjusting the degree of threading of each target 560, 562 onto the corresponding forceps tine. In other words, the height of each target is preferably not fixed, and may be increased for instance by counterclockwise turns as appropriate if observed by fibular plate fixation.

These targets 560, 562 are specifically designed to eliminate subjective judgements of surgeons, by providing precise identification of the desired axis (20-30 degrees from the coronal plane) with internal rotation of the limb, resulting in super-imposition of the two targets. The desired axis is now parallel to the operating room table with the patient in a supine position, allowing consistent, accurate and reproducible fixation device insertion by the surgeon. This eliminates the subjective errors resulting from rotation of the patient's limbs, which affects the optimal fixation device trajectory along the transmalleolar/centroidal axis, resulting in iatrogenic sagittal/axial syndesmotic reduction.

Figure 14:
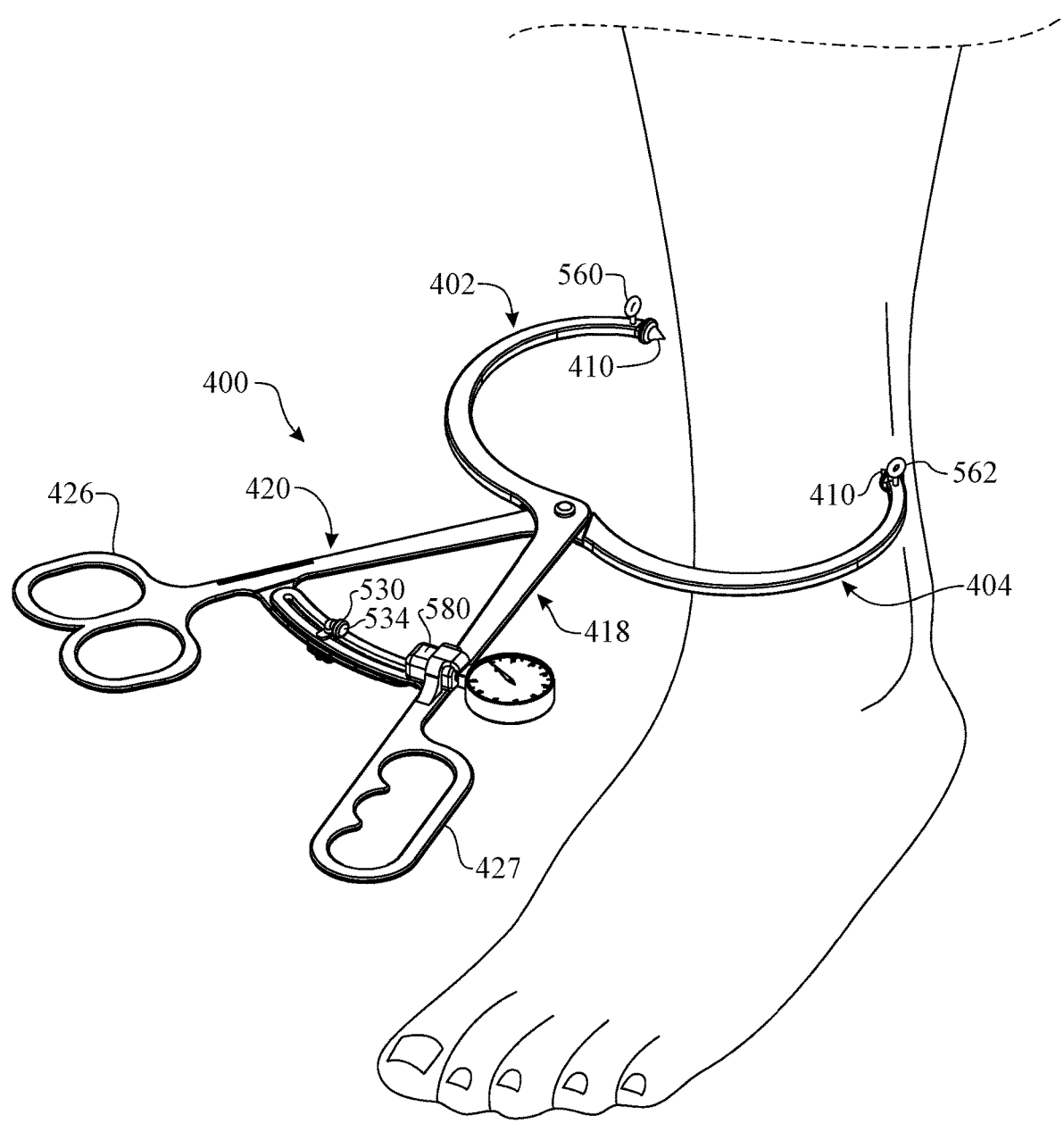
FIG. 14 presents a first step of an illustrative method of operation of the force-limiting forceps of FIG. 9.

An example of operation of the axis aligning, force-limiting forceps 400 will now be discussed with reference to FIGS. 14 and 15. The patient is placed in a supine position on the operating room table. The lateral forceps tine 404 of the reduction clamp or force-limiting forceps 400 is placed on the lateral peroneal/malleolar ridge of the fibula approximately 10-20 mm proximal to the distal/tibial plafond. A true talar dome lateral image is then obtained under fluoroscopy by the operating surgeon, using a fluoroscopy unit (not shown). The medial forceps tine 402 of the axis aligning, force-limiting forceps 400 is then positioned just anterior to the midline of the medial tibias surface (approximately 4 mm anterior to the midline), located anterior to the anterior border of the fibula, or in the junction of the anterior ⅓ and central ⅓ of the medial tibias width (if the medial surface is divided into 3 s). This is performed under fluoroscopic assistance.

Next, an appropriate reduction force is applied by compressing the lateral and medial forceps handles 418 and 420 towards one another. The force quantifying and limiting mechanism 470 assists the surgeon in applying said appropriate reduction force. Specifically, as shown in FIG. 15, upon compressing the lateral and medial forceps handles 418 and 420 towards one another, the pusher end 534 of the pusher 530 pushes the button 498 of the mechanical pressure gauge 580 inward, i.e. into the housing 582 and towards the fluid 486. As understood from FIGS. 16 and 18, this causes the second portion 502 of the button 498 to apply pressure to the fluid 486 housed within the internal fluid chamber 484 of the pressure gauge 480. The compressed fluid 486 displaces the piston 488, causing the piston shaft 494 to displace and cause the rotation of the pointer 516 via the internal gear assembly 512. Movement of the pointer 516 along the visual markings 518 of the dial 510 allows the surgeon to monitor the magnitude of the reduction force being applied by the axis aligning, force-limiting forceps 400. When the appropriate reduction force is reached, the surgeon can tighten the nut 542 (FIG. 12) to prevent sliding of the pusher 530 along the second slot 526 of the second arm 522, i.e. to lock the lateral and medial forceps handles 418 and 420, and thus the tine tips 410, in place relative to one another, and thus to fix the position of the pusher 530 against the button 498.

Maintaining the true talar dome lateral positioning of the limb under fluoroscopy, and with the axis aligning, force-limiting forceps 400 applied firmly in place, the surgeon carefully internally rotates the limb until the circular target 562 located on the dorsal aspect of the lateral forceps tine 404 aligns directly in line with the target 560 located dorsally on the medial forceps tine 402. The desired transmalleolar/centroidal axis, as defined by the surgeon's placement of the clamp tines, has now been identified and aligned parallel to the coronal plane of the limb and parallel to the operating room table. Fixation devices (not shown) may then be applied directly perpendicular to the longitudinal axis of the fibula, and tibia from lateral to medial more proximally, in parallel to the superimposed targets more distally, and parallel to the operating room table, eliminating the subjective judgement of the surgeon in attempting to aim fixation devices along the desired axis (20-30 degrees) from other positions of rotation, using commercially available devices. If needed, due to obstruction of the targets 560, 562 by plate fixation, both targets 560, 562 may be adjusted (e.g., turned counterclockwise) to increase their height, allowing visualization through one of the plates' empty holes. Following the rotation step, either or both targets 560, 562 may be removed if obstructing fixation device insertion. Following fixation device insertion, the surgeon may loosen the nut 542 and open and remove the force-limiting forceps 400. The limb may thus be released and allowed to re-rotate back to its position of external rotation. Fixation along the desired transmalleolar/centroidal axis standardized by the targeting guide system may then be verified.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A reduction forceps suitable for the reduction and realignment of specific anatomic structures, comprising:
    a medial forceps tine and a lateral forceps tine;
    a pair of tine tips terminating the medial and lateral forceps tines, respectively;
    a lateral forceps handle and a medial forceps handle extending from the medial forceps tine and lateral forceps tine, respectively;
    a first tine/handle junction attaching the lateral forceps handle to the medial forceps tine;
    a second tine/handle junction attaching the medial forceps handle to the lateral forceps tine, the second tine/handle junction pivotally attached to the first tine/handle junction about a rotation axis; and
    a force quantifying and limiting mechanism configured to limit the magnitude of clamping force applied by the medial and lateral forceps tines, the force quantifying and limiting mechanism comprising a mechanical pressure gauge and a pusher, wherein the mechanical pressure gauge is configured to be actuated responsively to pivoting the medial forceps handle and lateral forceps handle relative to one another about the rotation axis, and the pusher is configured to push a button on the mechanical pressure gauge responsively to pivoting the medial forceps handle and lateral forceps handle toward one another about the rotation axis, and further wherein an angular distance between the pusher and the mechanical pressure gauge is adjustable, wherein the mechanical pressure gauge is carried by one of the lateral forceps handle and the medial forceps handle, and the pusher is carried by a first arc-shaped arm comprised in the other of the lateral forceps handle and the medial forceps handle, wherein the first arc-shaped arm extends towards the mechanical pressure gauge; wherein
    said one of the lateral forceps handle and the medial forceps handle comprises a second arc-shaped arm disposed overlapping the first arc-shaped arm, and further wherein the first and second arc-shaped arms are interlockable with one another to prevent a relative movement thereof and thereby prevent rotation of the medial and lateral forceps tines and the lateral and medial forceps handles about the rotation axis.

2. The reduction forceps of claim 1, wherein the mechanical pressure gauge is carried by one of the lateral forceps handle and the medial forceps handle, and the pusher is carried by the other of the lateral forceps handle and the medial forceps handle.

3. The reduction forceps of claim 1, wherein the mechanical pressure gauge is carried by the lateral forceps handle and the pusher is carried by the medial forceps handle.

4. The reduction forceps of claim 1, wherein the position of the pusher along the first arc-shaped arm is adjustable to vary the angular distance between the pusher and the mechanical pressure gauge.

5. The reduction forceps of claim 1, wherein the pusher comprises a pusher body and an attachment plate, the pusher body extending through the first and second arc-shaped arms and comprising a shoulder portion, wherein the shoulder portion and attachment plate are arranged on opposite sides of the first and second arc-shaped arms and configured to press against the first and second arc-shaped arms and frictionally prevent a relative movement of the first and second arc-shaped arms.

6. The reduction forceps of claim 5, wherein the first and second arc-shaped arms comprise respective first and second arc-shaped slots, wherein the first and second arc-shaped slots overlap with one another, and further wherein the pusher body extends through the first and second arc-shaped slots.

7. The reduction forceps of claim 6, wherein the pusher is fixable at different angular positions along the second arc-shaped slot to vary the angular distance between the pusher and the mechanical pressure gauge.

8. The reduction forceps of claim 7, wherein the second arc-shaped arm comprises a set of angularly-spaced-apart openings and the pusher is selectively fixable to different openings to vary the angular distance between the pusher and the mechanical pressure gauge.

9. The reduction forceps of claim 1, further comprising a pair of target portions arranged at the tine tips, wherein the target portions are visible by X-ray imaging.

10. The reduction forceps of claim 9, wherein the target portions are oriented such that the target portions are aligned in a direction parallel to a direction of alignment of the tine tips.

11. The reduction forceps of claim 9, wherein at least one of the target portions is height-adjustable.

12. The reduction forceps of claim 9, wherein at least one of the target portions is removable from the corresponding tine tip.

13. The reduction forceps of claim 1, wherein the force quantifying and limiting mechanism comprises a visual indicator of the magnitude of clamping force applied by the medial and lateral forceps tines.

14. A reduction forceps suitable for the reduction and realignment of specific anatomic structures, comprising:
a medial forceps tine and a lateral forceps tine;
a pair of tine tips terminating the medial and lateral forceps tines, respectively;
a lateral forceps handle and a medial forceps handle extending from the medial forceps tine and lateral forceps tine, respectively;
a first tine/handle junction attaching the lateral forceps handle to the medial forceps tine;
a second tine/handle junction attaching the medial forceps handle to the lateral forceps tine, the second tine/handle junction pivotally attached to the first tine/handle junction about a rotation axis; and
a force quantifying and limiting mechanism configured to limit the magnitude of clamping force applied by the medial and lateral forceps tines, the force quantifying and limiting mechanism comprising a visual indicator of the magnitude of clamping force applied by the medial and lateral forceps tines, the force quantifying and limiting mechanism comprising a mechanical pressure gauge and a pusher, wherein the mechanical pressure gauge is configured to be actuated responsively to pivoting the medial forceps handle and lateral forceps handle relative to one another about the rotation axis, and the pusher is configured to push a button on the mechanical pressure gauge responsively to pivoting the medial forceps handle and lateral forceps handle toward one another about the rotation axis, and further wherein an angular distance between the pusher and the mechanical pressure gauge is adjustable, wherein the mechanical pressure gauge is carried by one of the lateral forceps handle and the medial forceps handle, and the pusher is carried by a first arc-shaped arm comprised in the other of the lateral forceps handle and the medial forceps handle, wherein the first arc-shaped arm extends towards the mechanical pressure gauge; wherein
the position of the pusher along the first arc-shaped arm is adjustable to vary the angular distance between the pusher and the mechanical pressure gauge.

15. A reduction forceps suitable for the reduction and realignment of specific anatomic structures, comprising:
a medial forceps tine and a lateral forceps tine;
a pair of tine tips terminating the medial and lateral forceps tines, respectively;
a lateral forceps handle and a medial forceps handle extending from the medial forceps tine and lateral forceps tine, respectively;
a first tine/handle junction attaching the lateral forceps handle to the medial forceps tine;
a second tine/handle junction attaching the medial forceps handle to the lateral forceps tine, the second tine/handle junction pivotally attached to the first tine/handle junction about a rotation axis; and
a force quantifying and limiting mechanism configured to limit the magnitude of clamping force applied by the medial and lateral forceps tines, the force quantifying and limiting mechanism comprising a visual indicator of the magnitude of clamping force applied by the medial and lateral forceps tines, the force quantifying and limiting mechanism comprising a mechanical pressure gauge and a pusher, wherein the mechanical pressure gauge is configured to be actuated responsively to pivoting the medial forceps handle and lateral forceps handle relative to one another about the rotation axis, and the pusher is configured to push a button on the mechanical pressure gauge responsively to pivoting the medial forceps handle and lateral forceps handle toward one another about the rotation axis, and further wherein an angular distance between the pusher and the mechanical pressure gauge is adjustable, wherein the mechanical pressure gauge is carried by one of the lateral forceps handle and the medial forceps handle, and the pusher is carried by a first arc-shaped arm comprised in the other of the lateral forceps handle and the medial forceps handle, wherein the first arc-shaped arm extends towards the mechanical pressure gauge; wherein
said one of the lateral forceps handle and the medial forceps handle comprises a second arc-shaped arm disposed overlapping the first arc-shaped arm, and further wherein the first and second arc-shaped arms are interlockable with one another to prevent a relative movement thereof and thereby prevent rotation of the medial and lateral forceps tines and the lateral and medial forceps handles about the rotation axis; and further wherein the reduction forceps is configured to adopt a locked position in which rotation of the medial and lateral forceps tines about the rotation axis is prevented by the force quantifying and limiting mechanism.

16. A reduction forceps suitable for the reduction and realignment of specific anatomic structures, comprising:

a medial forceps tine and a lateral forceps tine;

a pair of tine tips terminating the medial and lateral forceps tines, respectively;

a lateral forceps handle and a medial forceps handle extending from the medial forceps tine and lateral forceps tine, respectively;

a first tine/handle junction attaching the lateral forceps handle to the medial forceps tine;

a second tine/handle junction attaching the medial forceps handle to the lateral forceps tine, the second tine/handle junction pivotally attached to the first tine/handle junction about a rotation axis; and a force quantifying and limiting mechanism configured to limit the magnitude of clamping force applied by the medial and lateral forceps tines, the force quantifying and limiting mechanism comprising a mechanical pressure gauge and a pusher, wherein the mechanical pressure gauge is configured to be actuated responsively to pivoting the medial forceps handle and lateral forceps handle relative to one another about the rotation axis, and the pusher is configured to push a button on the mechanical pressure gauge responsively to pivoting the medial forceps handle and lateral forceps handle toward one another about the rotation axis, and further wherein an angular distance between the pusher and the mechanical pressure gauge is adjustable, wherein the mechanical pressure gauge is carried by one of the lateral forceps handle and the medial forceps handle, and the pusher is carried by a first arc-shaped arm comprised in the other of the lateral forceps handle and the medial forceps handle, wherein the first arc-shaped arm extends towards the mechanical pressure gauge; wherein the position of the pusher along the first arc-shaped arm is adjustable to vary the angular distance between the pusher and the mechanical pressure gauge.

17. A reduction forceps suitable for the reduction and realignment of specific anatomic structures, comprising:

a medial forceps tine and a lateral forceps tine;

a pair of tine tips terminating the medial and lateral forceps tines, respectively;

a lateral forceps handle and a medial forceps handle extending from the medial forceps tine and lateral forceps tine, respectively;

a first tine/handle junction attaching the lateral forceps handle to the medial forceps tine;

a second tine/handle junction attaching the medial forceps handle to the lateral forceps tine, the second tine/handle junction pivotally attached to the first tine/handle junction about a rotation axis; and a force quantifying and limiting mechanism configured to limit the magnitude of clamping force applied by the medial and lateral forceps tines, the force quantifying and limiting mechanism comprising a visual indicator of the magnitude of clamping force applied by the medial and lateral forceps tines, the force quantifying and limiting mechanism comprising a mechanical pressure gauge and a pusher, wherein the mechanical pressure gauge is configured to be actuated responsively to pivoting the medial forceps handle and lateral forceps handle relative to one another about the rotation axis, and the pusher is configured to push a button on the mechanical pressure gauge responsively to pivoting the medial forceps handle and lateral forceps handle toward one another about the rotation axis, and further wherein an angular distance between the pusher and the mechanical pressure gauge is adjustable, wherein the mechanical pressure gauge is carried by one of the lateral forceps handle and the medial forceps handle, and the pusher is carried by a first arc-shaped arm comprised in the other of the lateral forceps handle and the medial forceps handle, wherein the first arc-shaped arm extends towards the mechanical pressure gauge; wherein the position of the pusher along the first arc-shaped arm is adjustable to vary the angular distance between the pusher and the mechanical pressure gauge; and further wherein the reduction forceps is configured to adopt a locked position in which rotation of the medial and lateral forceps tines about the rotation axis is prevented by the force quantifying and limiting mechanism.

* * * * *